US010092658B2

(12) United States Patent
Hahn et al.

(10) Patent No.: US 10,092,658 B2
(45) Date of Patent: Oct. 9, 2018

(54) METHOD FOR MANUFACTURING TRANSDERMALLY DELIVERED HYALURONIC ACID-PROTEIN CONJUGATE AND TRANSDERMALLY DELIVERED HYALURONIC ACID-PROTEIN CONJUGATE MANUFACTURED USING SAME

(71) Applicant: PHI BioMed Co., Ltd., Seoul (KR)

(72) Inventors: Sei Kwang Hahn, Pohang-si (KR); Eung-Sam Kim, Pohang-si (KR); Jeonga Yang, Pohang-si (KR); Hyemin Kim, Pohang-si (KR); Kwan Yong Choi, Pohang-si (KR); Ji Hye Shin, Daegu (KR); Jung-Hee Kwon, Pohang-si (KR)

(73) Assignee: PHI BIOMED CO., LTD., Seoul (KR)

( * ) Notice: Subject to any disclaimer, the term of this patent is extended or adjusted under 35 U.S.C. 154(b) by 0 days.

(21) Appl. No.: 14/376,202

(22) PCT Filed: Feb. 7, 2013

(86) PCT No.: PCT/KR2013/001002
§ 371 (c)(1),
(2) Date: Oct. 6, 2014

(87) PCT Pub. No.: WO2013/119061
PCT Pub. Date: Aug. 15, 2013

(65) Prior Publication Data

US 2015/0056254 A1 Feb. 26, 2015

(30) Foreign Application Priority Data

Feb. 7, 2012 (KR) ........................ 10-2012-0012315

(51) Int. Cl.

| | |
|---|---|
| ***A61K 47/36*** | (2006.01) |
| ***A61K 47/48*** | (2006.01) |
| ***C07K 17/10*** | (2006.01) |
| ***C08B 37/08*** | (2006.01) |
| ***C08H 1/00*** | (2006.01) |
| ***C08L 5/08*** | (2006.01) |
| ***C08L 89/00*** | (2006.01) |
| ***A61K 8/64*** | (2006.01) |
| ***A61K 8/73*** | (2006.01) |
| ***A61K 38/27*** | (2006.01) |
| ***A61K 39/00*** | (2006.01) |
| ***A61Q 19/00*** | (2006.01) |
| ***C07K 14/61*** | (2006.01) |
| ***A61K 47/61*** | (2017.01) |

(52) U.S. Cl.
CPC ............ *A61K 47/4823* (2013.01); *A61K 8/64* (2013.01); *A61K 8/735* (2013.01); *A61K 38/27* (2013.01); *A61K 39/00* (2013.01); *A61K 47/61* (2017.08); *A61Q 19/00* (2013.01); *C07K 14/61* (2013.01); *C07K 17/10* (2013.01); *C08B 37/0072* (2013.01); *C08H 1/00* (2013.01); *C08L 5/08* (2013.01); *C08L 89/00* (2013.01); *A61K 2039/6087* (2013.01); *A61K 2800/57* (2013.01); *A61K 2800/91* (2013.01)

(58) Field of Classification Search
None
See application file for complete search history.

(56) References Cited

U.S. PATENT DOCUMENTS 7,714,114 B2 * 5/2010 Bossard ........... A61K 47/48215 424/78.38
2013/0253170 A1 * 9/2013 Hahn ................. A61K 47/4823 530/351

FOREIGN PATENT DOCUMENTS

| | | | |
|---|---|---|---|
| CA | 2821075 | | 6/2012 |
| JP | 2003-535144 | | 11/2003 |
| JP | 2005-508854 | | 4/2005 |
| JP | 2006-500324 | | 1/2006 |
| JP | 2011-526799 | | 10/2011 |
| WO | WO 01/05434 | * | 1/2001 |
| WO | 2003/094929 | | 11/2003 |
| WO | 2011/069474 | | 6/2011 |
| WO | WO 2012/077950 | * | 6/2012 |

OTHER PUBLICATIONS

Badkar et al ('Transdermal delivery of interferon alpha-2b using microporation and iontophoresis in hairless rats' Pharmaceutical Research v24(7) Jul. 2007 pp. 1389-1395).*
Word Press (retrieved from https://chewychunks.wordpress.com/2015/01/30/why-two-thirds-of-cancer-cases-are-not-preventable/ on Jun. 30, 2015, 4 pages).*
Home Vet (retrieved from http://www.homevet.com/pet-care-library/item/382-what-are-the-signs-of-cancer-in-pets on Jun. 30, 2015, 3 pages).*
Kaldas Center (retrieved from http://kaldascenter.com/media/Kaldas-Center-Breast-Cancer.pdf on Jun. 30, 2015, 1 page).*
UICC (retrieved from http://www.uicc.org/programmes/childhood-cancer on Jun. 30, 2015, 1 page).*

(Continued)

*Primary Examiner* — Karlheinz R. Skowronek
*Assistant Examiner* — Ronald T Niebauer
(74) *Attorney, Agent, or Firm* — Lex IP Meister, PLLC

(57) ABSTRACT

A transdermal delivery system of drug and a method of preparing the same are provided. More specifically, the invention can be a transdermal delivery system applied for various protein drugs such as vaccines and chemical drugs, because the drug delivery system has a biocompatibility, biodegradation property, transdermal delivery property, the safety of human body, maximum activity of protein drugs, good bio-conjugation efficiency and a long-term efficacy, a method of preparing the same and its use.

6 Claims, 12 Drawing Sheets

(56) References Cited

OTHER PUBLICATIONS

CheckOrphan (retrieved from http://www.checkorphan.org/diseases/dwarfism on Jul. 6, 2015, 2 pages).*

Definition of dark (retrieved from http://www.thefreedictionary.com/dark on Jul. 7, 2015, 10 pages).*

Yang, J.-A. et al., "Target specific hyaluronic acid-interferon alpha conjugate for the treatment of hepatitis C virus infection", Biomaterials, Nov. 2011, vol. 32, No. 33, pp. 8722-8729.

Brown, T. J. et al., "Absorption of hyaluronan applied to the surface of intact skin", J. Invest. Dermatol., Nov. 1999, vol. 113, No. 5, pp. 740-746.

Raja, R. H. et al., "Preparation of alkylamine and 125l-radiolabeled derivatives of hyaluronic acid uniquely modified at the reducing end", Anal. Biochem., May 15, 1984, vol. 139, No. 1, pp. 168-177.

Yeo, Y. et al., "In situ cross-linkable hyaluronic acid hydrogels prevent post-operative abdominal adhesions in a rabbit model", Biomaterials, Sep. 2006, vol. 27, No. 27, pp. 4698-4705.

Basavaragj, K.H. et al, "Biopolymers as transdermal drug delivery systems in dermatology therapy", Crit Rev Ther Drug Carrier Syst., 27(2), pp. 155-185, Abstract only; From PubMed; PMID: 20499487, Jan. 2010.

The Office Action and the Examination Search Report, Canadian Intellectual Property Office, Oct. 23, 2015, Application No. 2,867,917.

Jeong-A Yang, et al., "Transdermal delivery of hyaluronic acid—Human growth hormone conjugate", Biomaterials, Elsevier Science Publishers BV., Barking, GB, vol. 33, No. 25, May 3, 2012, pp. 5947-5954.

L S Zhang, et al., "Development of a hyaluronan bioconjugate for the topical teatment of melanoma", Journal of Dermatological Science, Elsevier Science Publishers, Shannon, IE, vol. 55, No. 1, Jul. 1, 2009, pp. 56-59.

The Extended European Search Report, dated Sep. 11, 2015, European Patent Application No. 13746520.9.

* cited by examiner

METHOD FOR MANUFACTURING TRANSDERMALLY DELIVERED HYALURONIC ACID-PROTEIN CONJUGATE AND TRANSDERMALLY DELIVERED HYALURONIC ACID-PROTEIN CONJUGATE MANUFACTURED USING SAME

FIELD OF THE INVENTION

The present invention relates to a transdermal drug delivery system and a method of preparing the same. More specifically, by using a drug delivery system having biocompatibility, biodegrading capacity and transdermal delivery capacity, the present invention provides a transdermal drug delivery system and a method of preparing the same which can be a safe delivery tool for various proteins, chemical drugs, and vaccines, and provides a most efficient transdermal drug delivery being capable of delivering a protein with a maximum bioactivity, a high bio-conjugation and a long-term efficacy.

DESCRIPTION OF THE RELATED ART

The transdermal delivery system is to deliver an effective component through skin, and has some advantages of no pain, self-administration, and treatment at any time.

However, there is a small amount of drug being capable of penetrating through the skin as a primary barrier to an external material, the transdermal delivery system has not been applied actively.

Therefore, in order to increase the amount being passed through the skim by improving the permeability of skin tissue barrier, a research by a patch system using microchip, and a transdermal drug delivery system has been actively performed by using external stimulus such as ultrasonic wave, electric field and the like.

The patch including minutely-molded microchip has a difficulty in the manufacture and a high cost. In case of the delivery system using the external stimulus for increasing the skin permeability, the advantages of transdermal delivery system may disappear due to the need of an apparatus and stimulus.

Accordingly, there is still need for a transdermal delivery system with a high skin permeability and an efficient transdermal drug delivery, without needing an apparatus or external stimulus.

SUMMARY OF THE INVENTION

With overcoming the problems of prior arts, the present invention provides a method of preparing a hyaluronic acid (HA)-protein conjugate, a HA-protein conjugate prepared therefrom and its use, where the HA-protein conjugate can be used as a transdermal drug delivery system which can maintain maximum bioactivity of protein drug and have a high bio-conjugation efficiency, and be applied for various water-soluble active components.

SUMMARY OF THE INVENTION

Figure 3A:
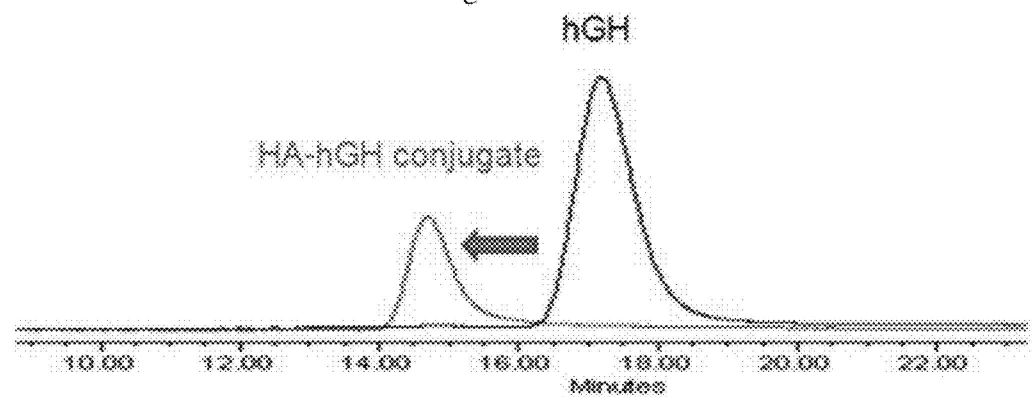
Figure 3B:
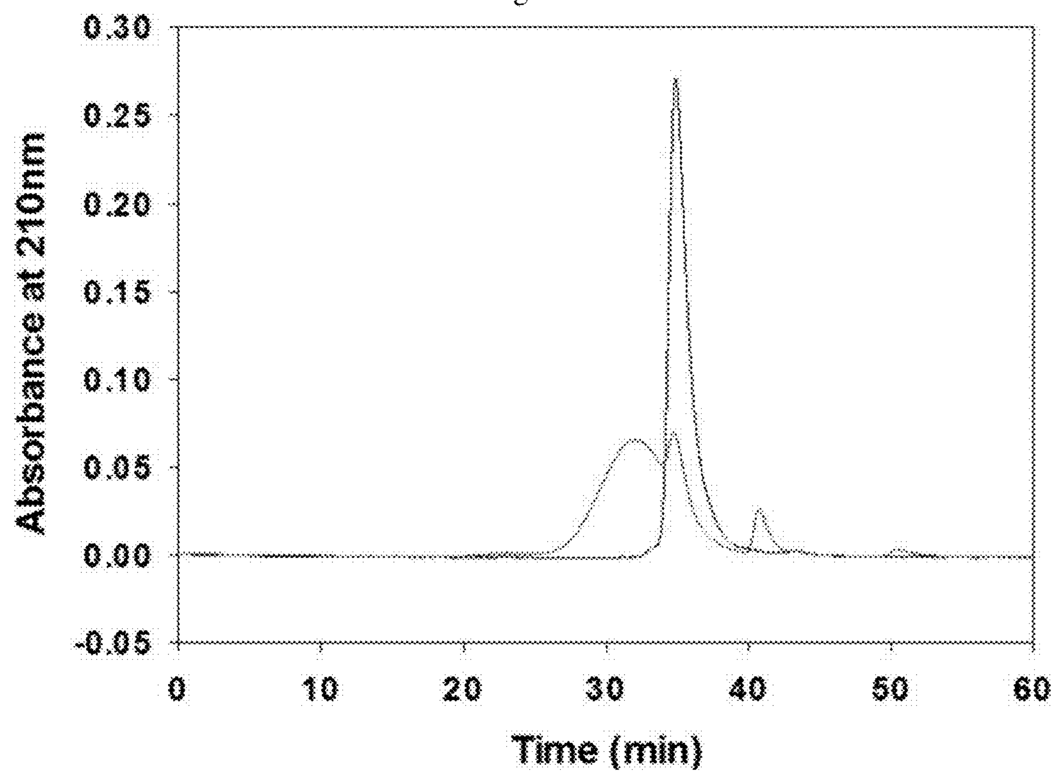

FIG. 3*a* is a GPC analysis result of a HA-human growth hormone (HA-hGH) conjugate and hGH which were prepared in Example 1, and FIG. 3*b* is a GPC analysis result of a HA-ovalbumin (HA-OVA) conjugate and OVA which were prepared in Example 2.

Figure 4:
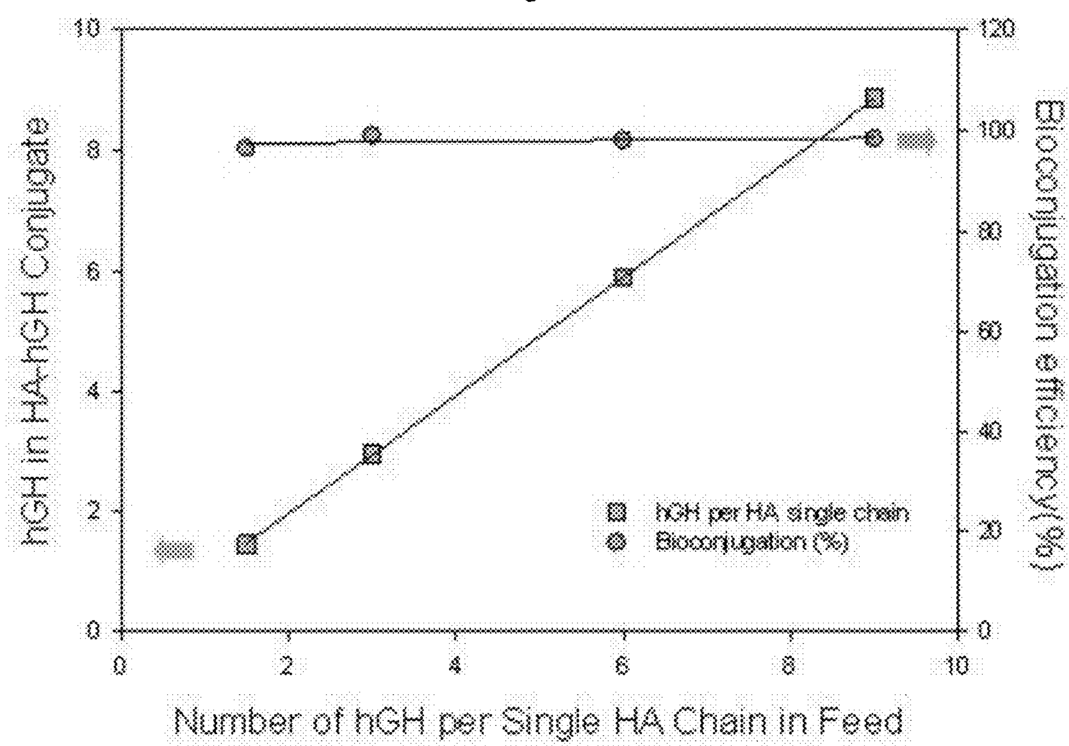

FIG. 4 shows the number of hGH molecules included in a HA of HA-hGH conjugate, and a bioconjugation efficiency depending on the number of hGH molecule.

Figure 5:
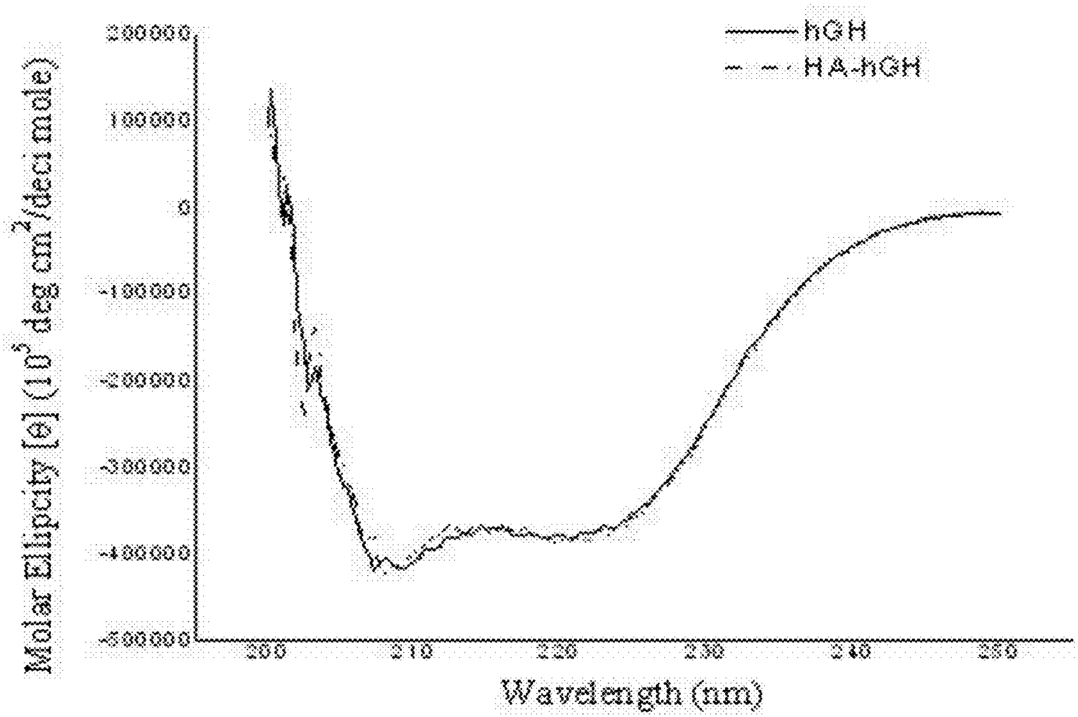

FIG. 5 is a Circular Dichroism, CD) analysis result comparing hGH with hyaluronic acid-hGH conjugate.

Figure 6A:
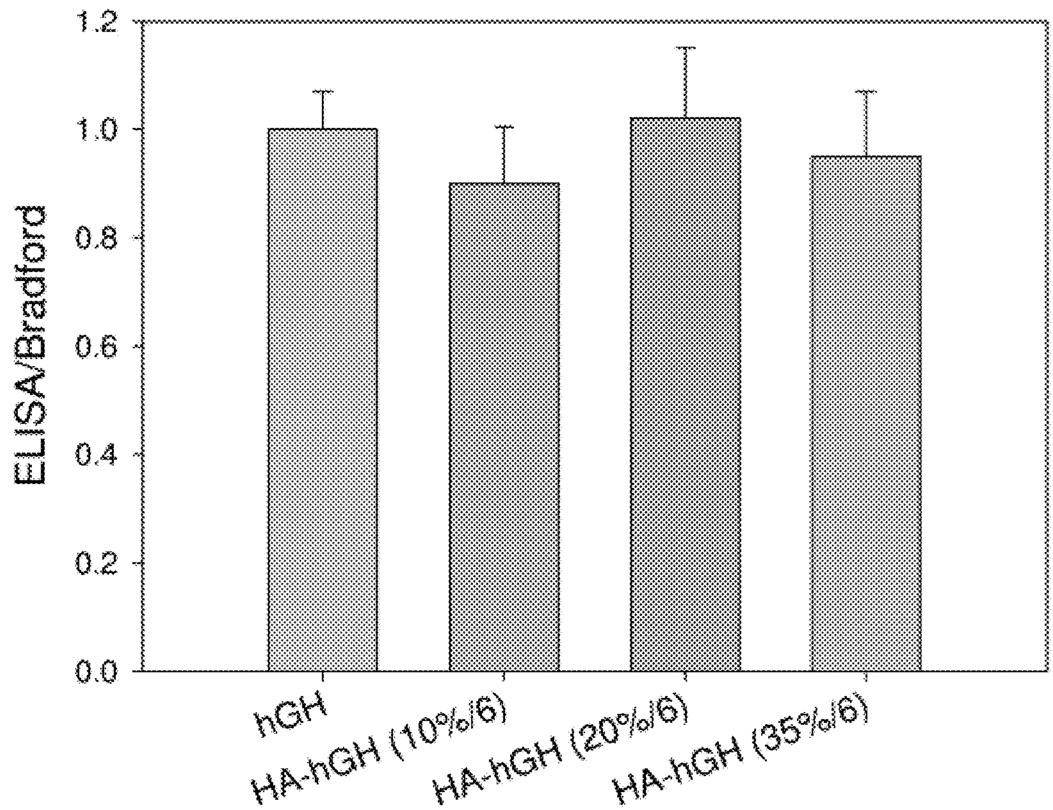
Figure 6B:
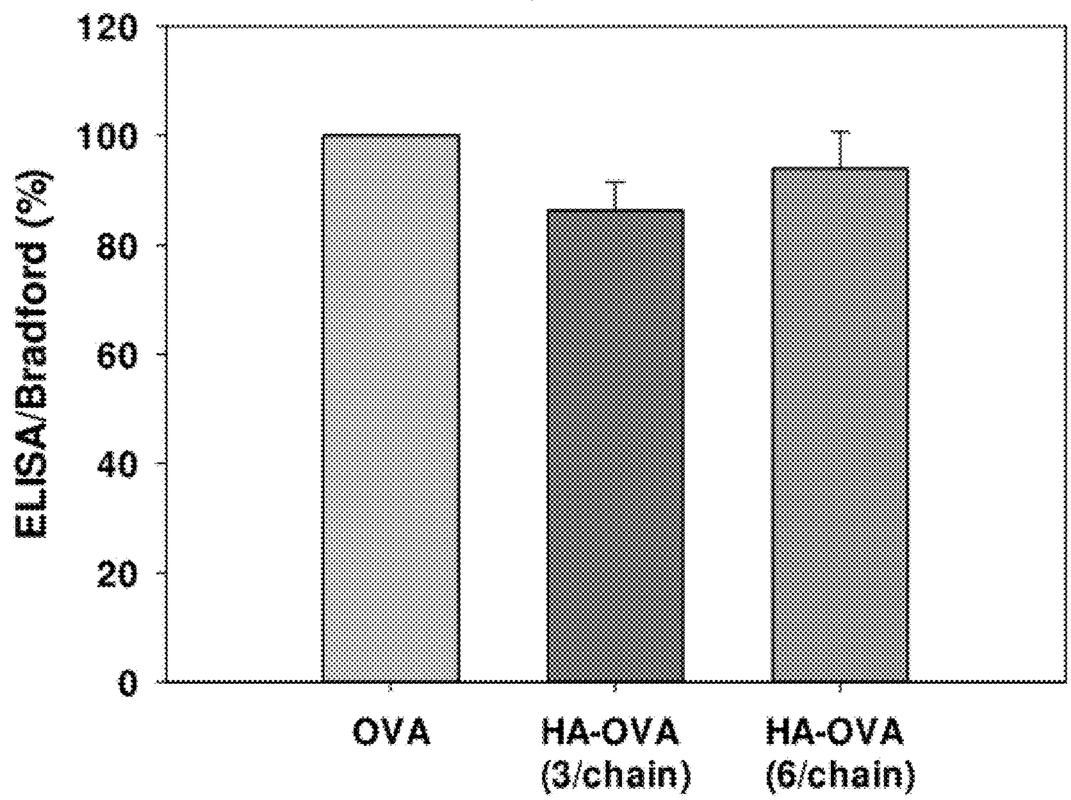

FIG. 6*a* is a ratio of ELISA/Bradford assay showing the activity analysis of HA-hGH conjugate and hGH obtained in Example 1, FIG. 6*b* is a ratio of ELISA/Bradford assay showing the activity analysis of HA-OVA conjugate and OVA obtained in Example 2.

Figure 7:
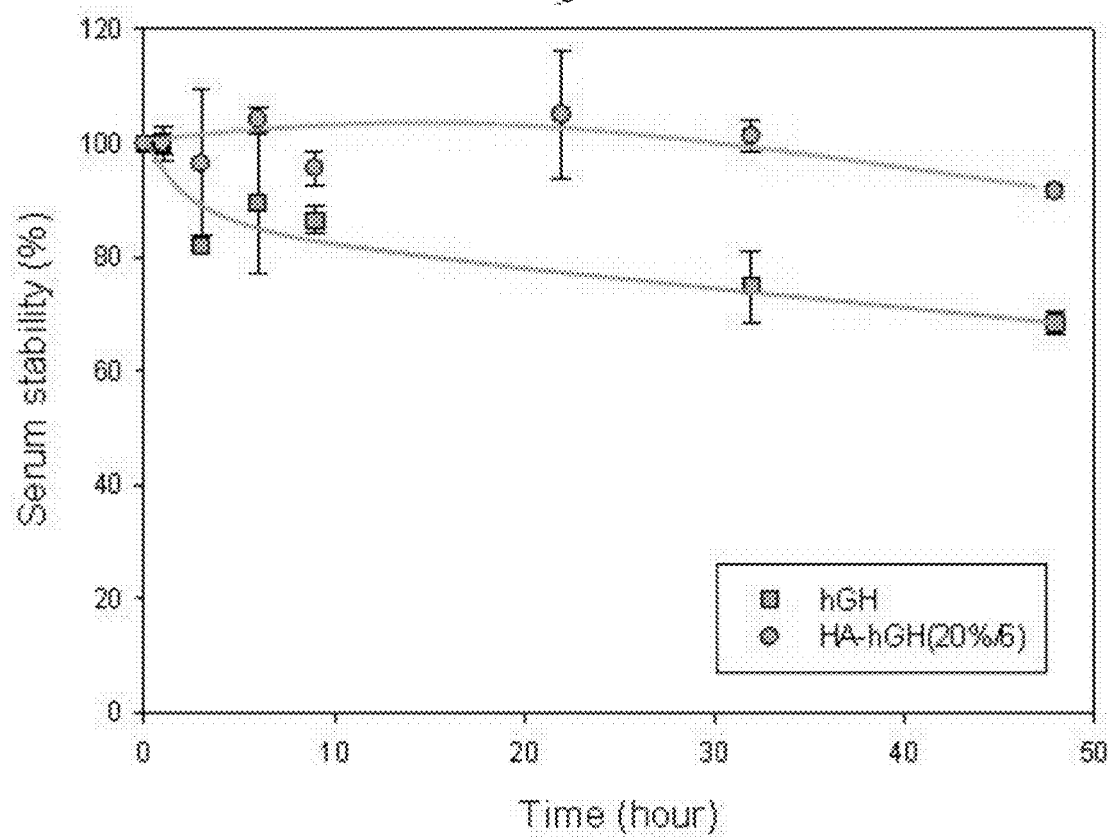

FIG. 7 is a stability in human serum of the HA-hGH conjugate and hGH obtained in Example 1.

Figure 8:
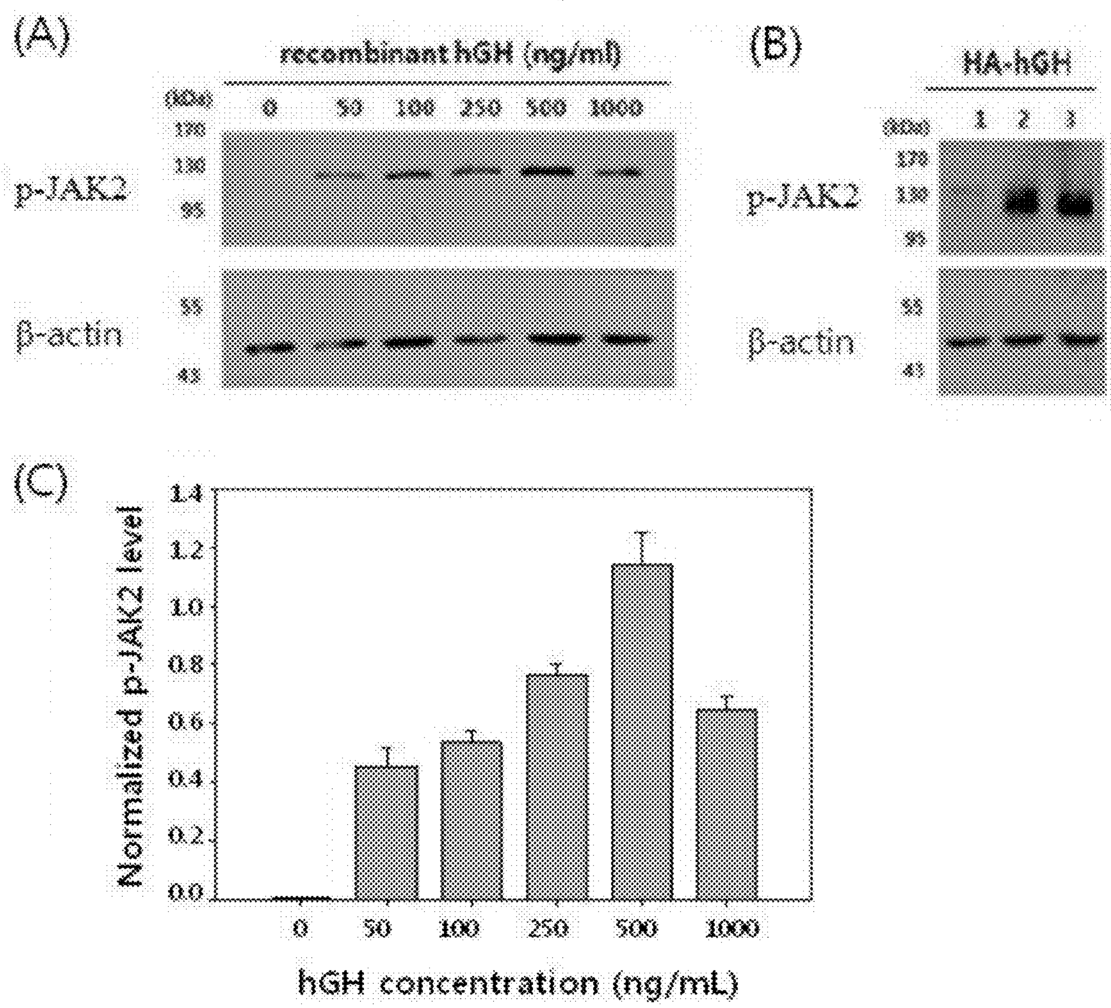

FIG. 8 is a cell signaling activity of HA-hGH conjugate and hGH in IM-9 cell (human B lymphoblast) (A: cell signal activity of the hGH measured at various concentrations of the hGH, B: cell signal activity of HA-hGH conjugate including 500 ng/ml hGH, C: quantitative analysis results of A and B band intensity.

Figure 9:
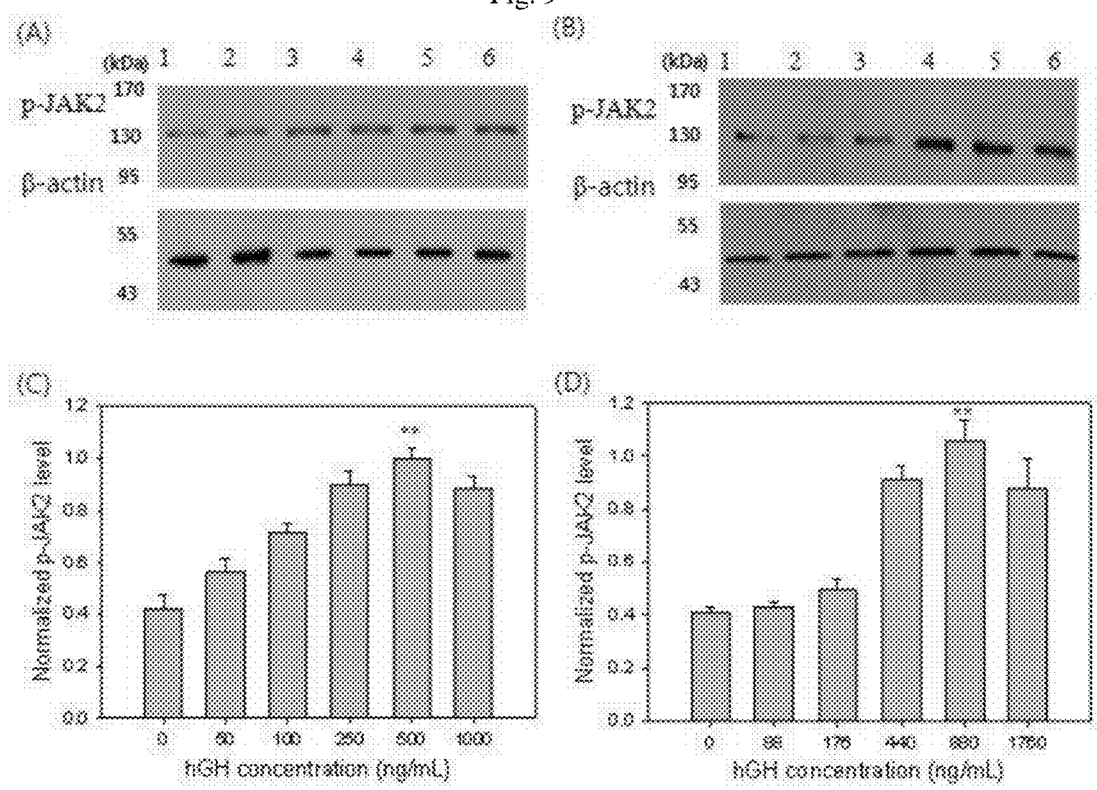

FIG. 9 shows JAK2 phosphorylation degree of the treatment of hGH and HA-hGH conjugate on human skin cell Detroit 551 (A: the result of cell signal activity of hGH receptor which was obtained from the measurement of JAK2 phosphorylation degree after treatment of hGH, B: the result of cell signal activity of hGH receptor which was obtained from the measurement of JAK2 phosphorylation degree after treatment of HA-hGH conjugate, C: quantitative analysis graph of A band intensity, D: quantitative analysis graph of B band intensity).

Figure 10:
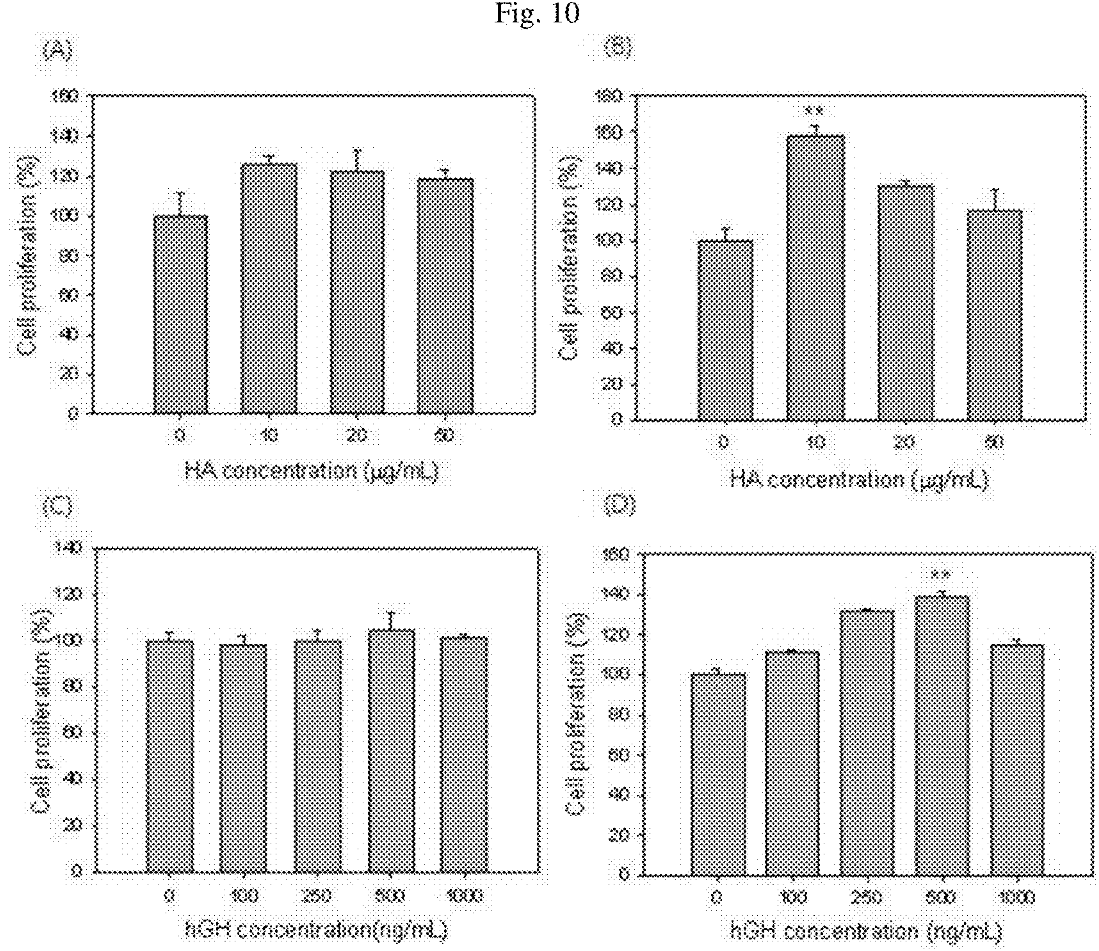

FIG. 10 shows cell growth effect of human skin cell (HEKn, Detroit 551) treated with hyaluronic acid and HA-hGH conjugate at various concentrations of HA and HA-hGH conjugate (A: cell growth effect of HEKn treated with various concentrations of HA, B: cell growth effect of Detroit 551 treated with various concentrations of HA, C: cell growth effect of HEKn treated with various concentrations of HA-hGH conjugate, D: cell growth effect of Detroit 551 treated with various concentrations of HA-hGH conjugate).

Figure 11:
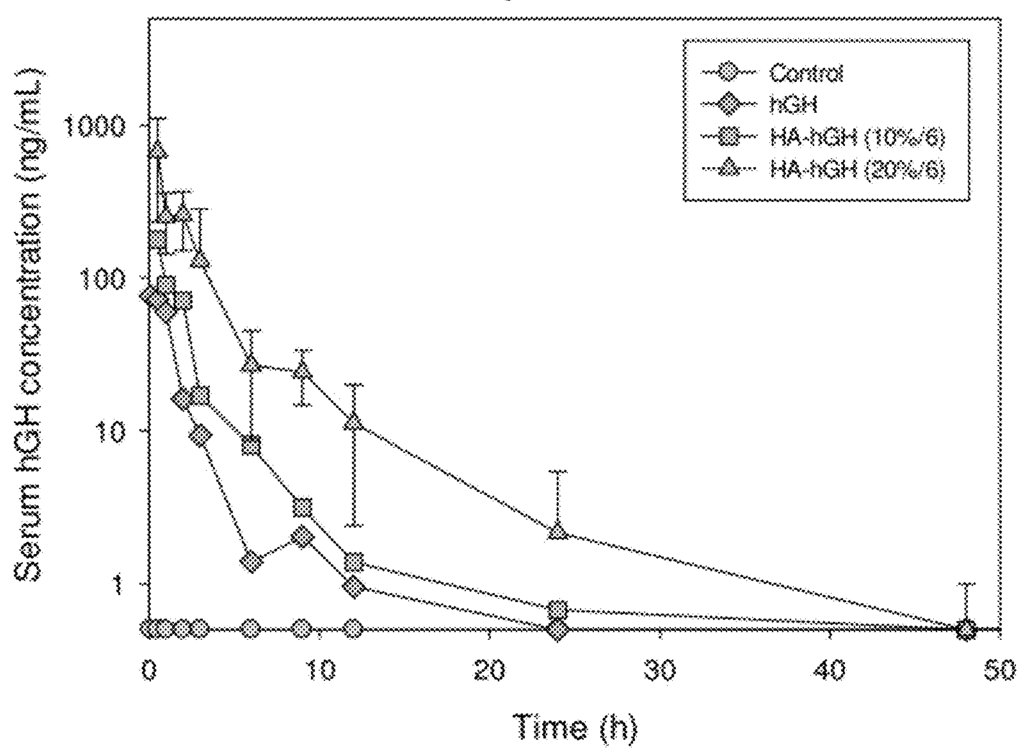

FIG. 11 shows a pharmacokinetic analysis result for i.v. injection of HA-hGH conjugate obtained in Example 1.

Figure 12:
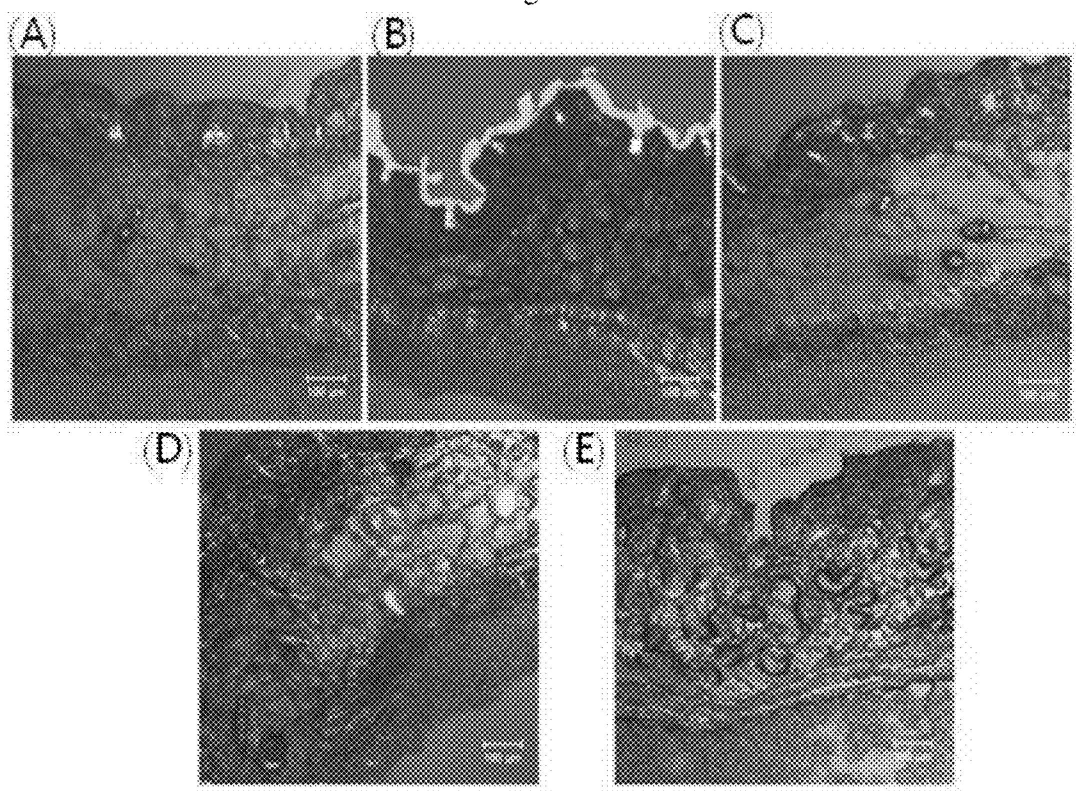

FIG. 12 shows a transdermal delivery activity analysis for HA-hGH conjugate, hGH and HA obtained in Example 1 (A: control, B: FITC, C: hGH-FITC, D: HA-FITC, E: HA-hGH-FITC).

Figure 13:
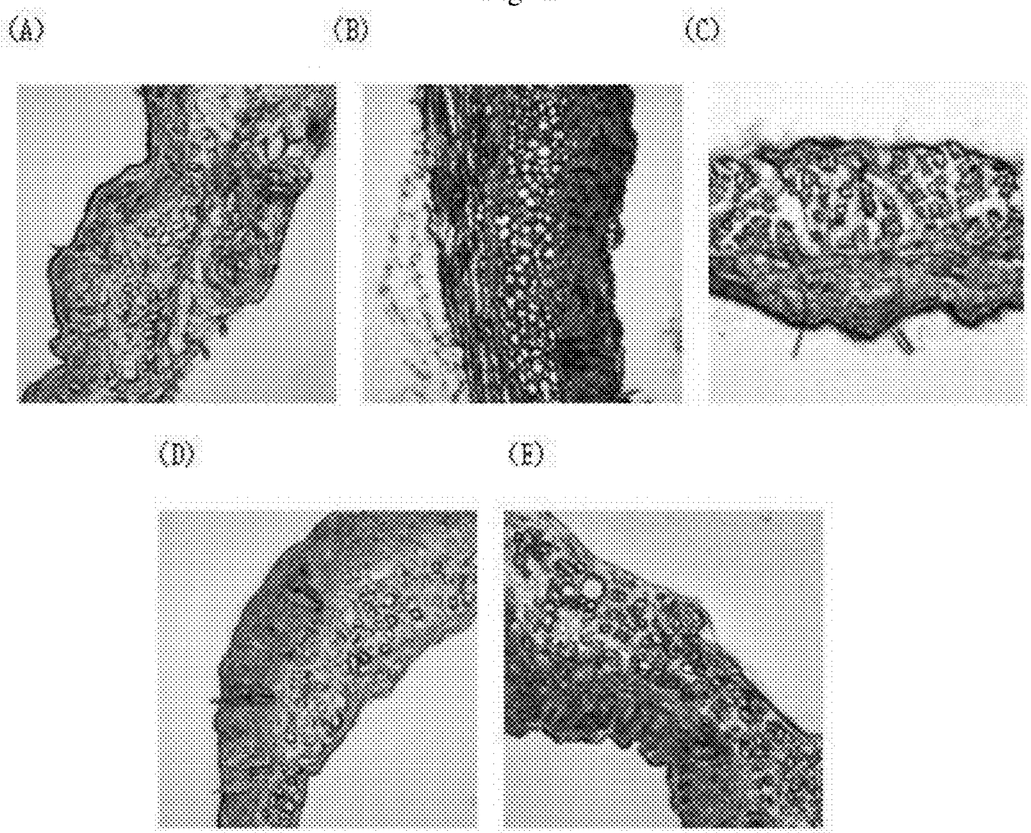

FIG. 13 shows a transdermal delivery activity analysis for HA-OVA conjugate, OVA and HA obtained in Example 2 (A: PBS, B: FITC, C: OVA-FITC, D: HA-FITC, E: HA-OVA-FITC).

Figure 14:
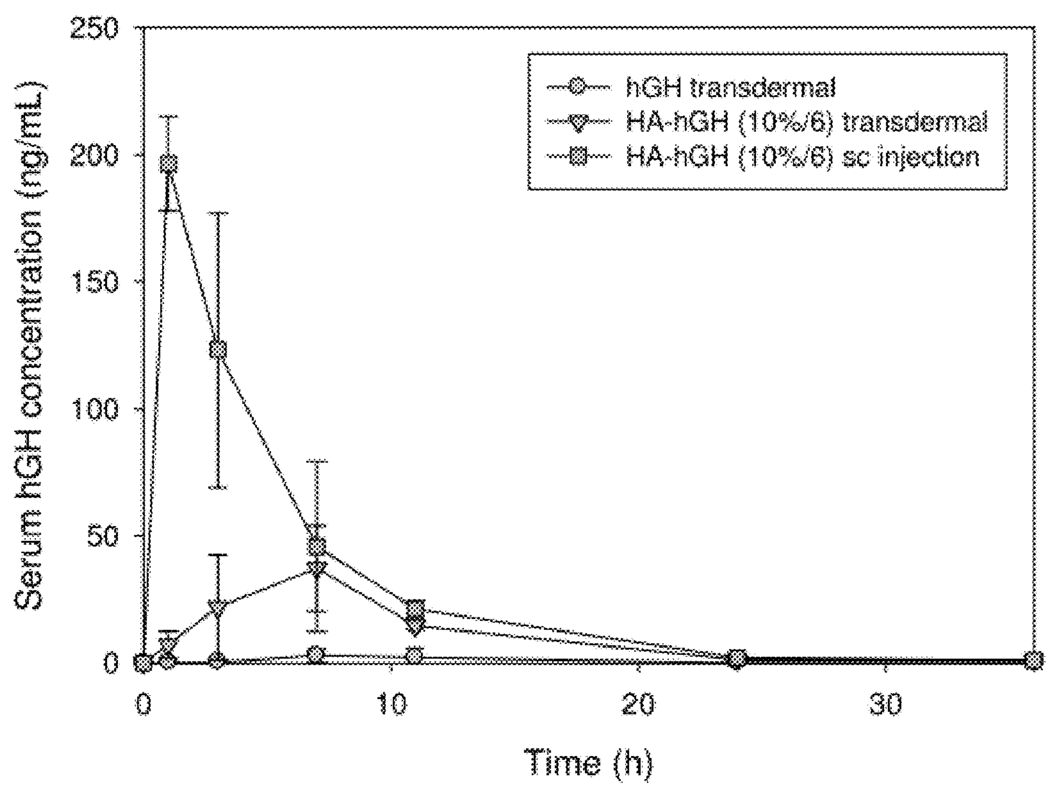

FIG. 14 shows a pharmacokinetic analysis result for i.v. injection of HA-hGH conjugate obtained in Example 1.

Figure 15:
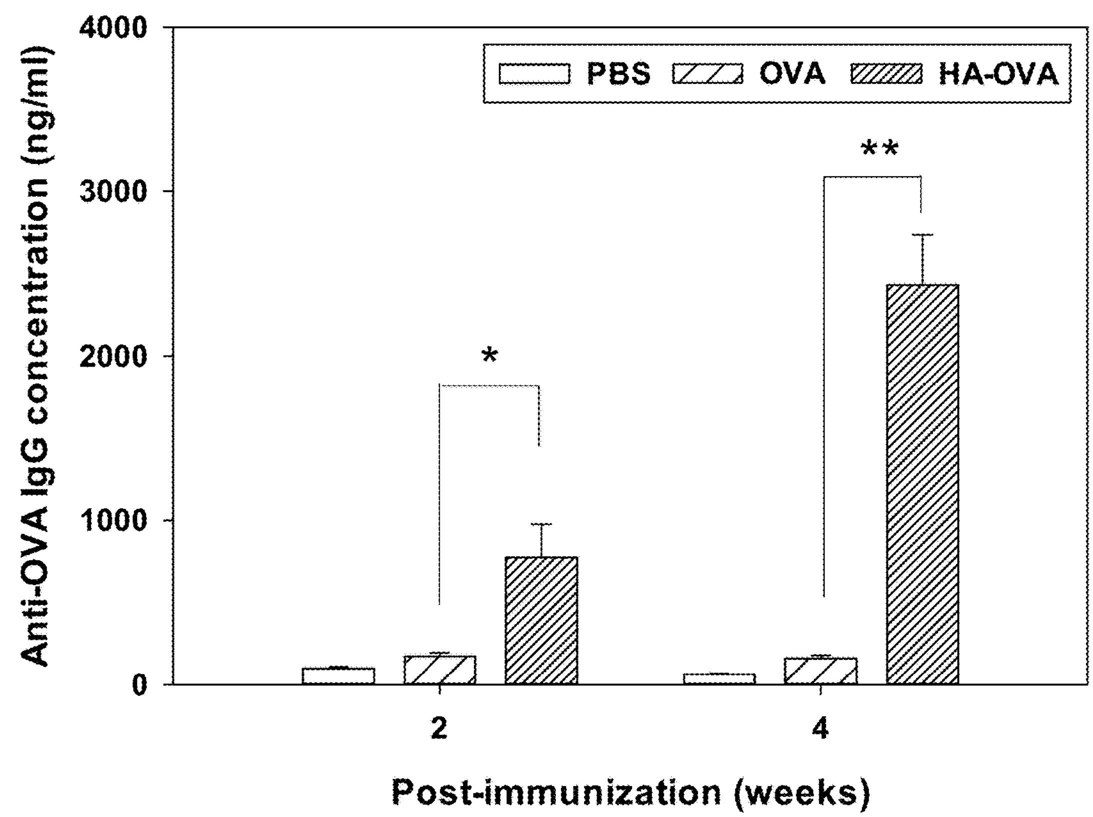

FIG. 15 shows a property of transdermal vaccine of HA-OVA conjugate obtained in Example 2, and an ELISA result of blood antibody concentration against OVA of PBS, OVA and HA-OVA, which was measured after 2 and 4 weeks of treatment.

DETAILED DESCRIPTION OF THE PREFERRED EMBODIMENTS

These and other objects of the invention will be more fully understood from the following description of the invention, the referenced drawings attached hereto and the claims appended hereto.

As the research, the present inventors found that the transdermal drug delivery system using hyaluronic acid could be used simpler than with a higher delivery efficiency than the injection, where the hyaluronic acid has an excellent transdermal capacity despite of its high molecular weight. In addition, the inventors found that the cell growth could be controlled by the concentration due to the present of HA receptor on the human skin and an useful for applications such as skin tissue regeneration and cosmetics. Especially, the present invention the conjugation of protein to be delivered to the hyaluronic acid is performed at a specific pH condition for preventing the reaction of other amino acid having an amine group such as lysine in the protein, thereby increasing the maximal activity, bioconjugation efficiency and efficacy-lasting time.

In accordance with an embodiment of the present invention, there is provided a method of preparing a hyaluronic acid-protein conjugate comprising a first step of preparing a hyaluronic acid-aldehyde (HA-aldehyde) as represented by Chemical formula 1; and a second step of reacting the hyaluronic acid-aldehyde with N-terminus of a water-soluble protein.

According to the method, a hyaluronic acid-protein conjugate represented by Chemical formula 2 is provided:

[Chemical formula 1]

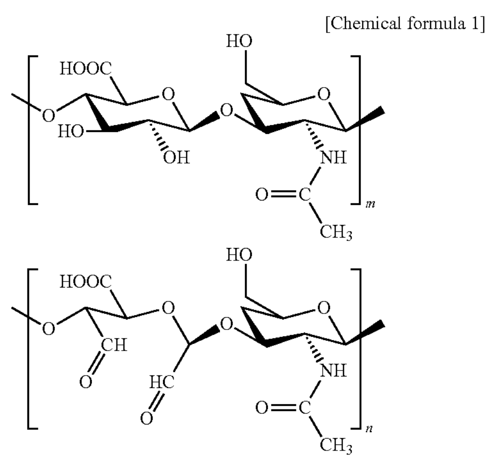

In chemical formula 1, the sum of m and n is an integer of 50 to 10,000, and n is an integer of 5 to 5,000.

[Chemical formula 2]

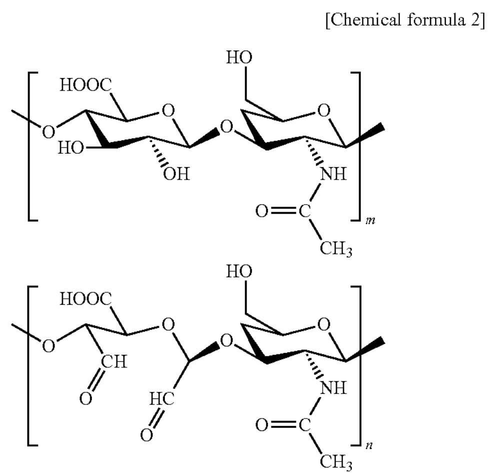

-continued

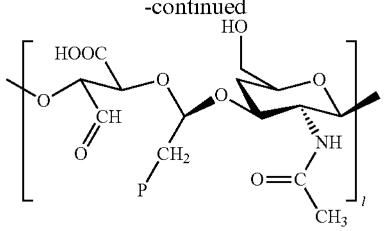

In chemical formula 2,

P is a water-soluble protein, the sum of m, n, and l is an integer of 50 to 10,000, the sum of n and l is an integer of 5 to 5,000, and l is an integer of 1 to 100.

Hereinafter, the hyaluronic acid-protein conjugate and the method of preparing the same will be described in more details in accordance with an embodiment of the present invention.

The hyaluronic acid of the present invention has various advantages of biocompatibility, biodegradation and transdermal delivery, and thus can be used safely in human body for transdermal delivery of various protein drugs and chemical drugs as well as antigen protein (Experimental Examples 8 to 13).

Herein, the term 'hyaluronic acid(Hyaluronic acid, HA), if otherwise not defined, refers to the polymer including a repeating unit represented by following chemical formula 1, a salt and a derivative thereof.

[Chemical formula 1]

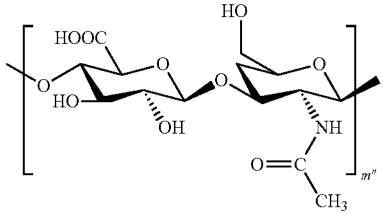

In Chemical formula 1, m is an integer of 50 to 10,000.

The term 'hyaluronic acid derivative' refers to all derivatives of hyaluronic acid where include a substituted groups such as amine group, aldehyde group, vinyl group, thiol group, allyloxy group, N-Succinimidyl-3-(2-pyridyldithio) propionates (SPDP), and N-hydroxysuccinimide (NHS) introduced to the basic backbone structure of hyaluronic acid, and the like. The examples of the derivatives of hyaluronic acid include HA-diaminobutane, HA-hexamethylenediamine, HA-aldehyde, HA-Adipic Acid Dihydrazide (HA-ADH), HA-2-Aminoethyl methacrylate hydrochloride, HA-Spermine, HA-spermidine, HA-SPDP, HA-NHS and the like.

The term, ' substitution ratio of carboxyl group(s)' means a mole ratio or a mole percentage of the repeating unit including substituted carboxyl group(s) relative to the entire repeating unit in the HA derivative. Thus, the substitution ratio can be greater than 0 but less than 1, or greater than 0 mole % but less than 100 mole %.

The HA used in the preparation of the HA derivatives exists mostly in animals, and is a polymer having biodegradable and biocompatible linear oligosaccharide without immunogenicity. Since HA plays a different role in the body depending on its molecular weight, it can serve various purposes.

In the process of preparing the hyaluronic acid-protein conjugate in accordance with the present invention, the useful hyaluronic acid, a salt of hyaluronic acid or a derivative of hyaluronic acid cannot be limited, and may have a molecular weight of 10,000 to 3,000,000 Da, preferably, which can be suitable for the conjugate of drug delivery system.

Hereinafter, the process of preparing hyaluronic acid-protein conjugate can be illustrated in more detail for each step by referring to Reaction scheme 1.

10 mole percent was substituted. When the oxidant was used at an 5 mole times for 12 hours, the product having 50 mole percent of substitution degree.

The reaction oxidant at an amount of the range can make HA-aldehyde derivative having substitution degree of 10 to 50 mole %. When the substitution degree is lower than the range, the low reacting amount of protein cannot achieve the desired effect. When the substitution degree is higher than the range, the HA-aldehyde derivative having an excessive high substitution has a difficulty in interaction with HA receptor, resulting in a low targeting effect.

[Reaction scheme 1]

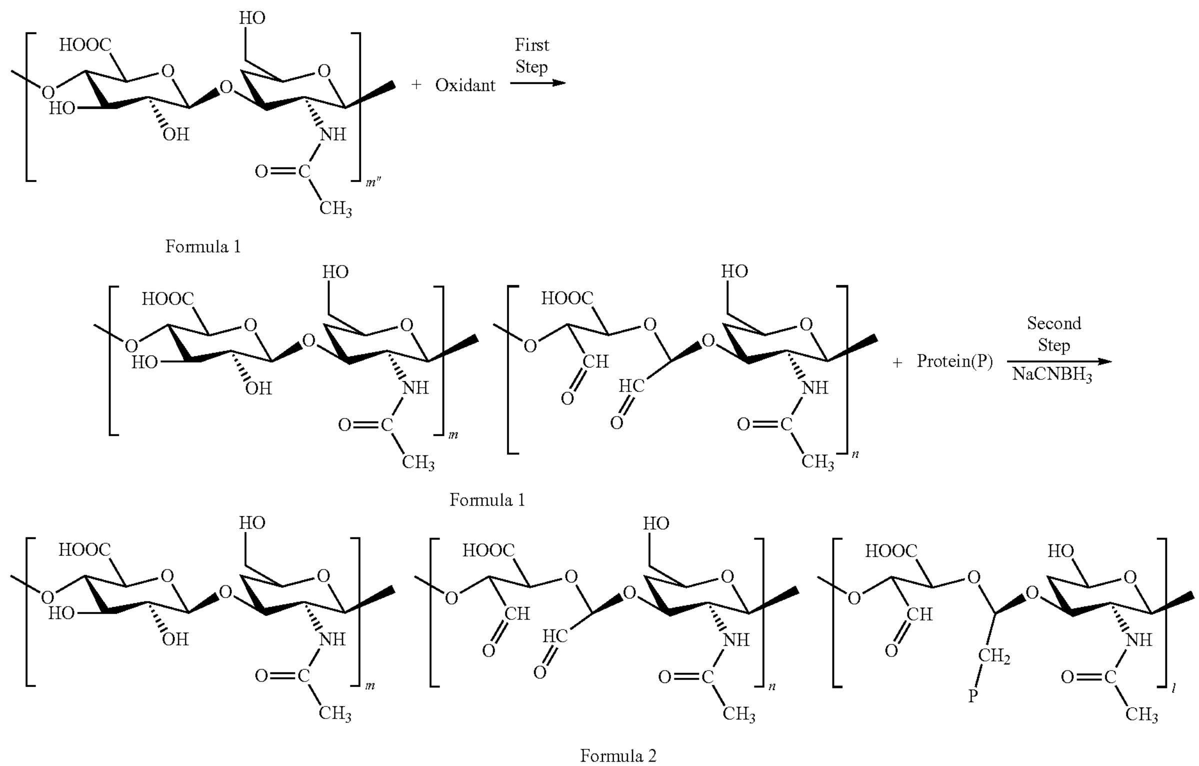

In Reaction scheme 1, m'', m, n, 1, and P are the same as defined in Chemical formula 1, Chemical formula 1, and Chemical formula 2.

The first step of preparing the hyaluronic acid-aldehyde (HA-aldehyde)(Chemical formula 1) is referred to the ring-opening reaction of cellulose, by dissolving hyaluronic acid (HA), a salt of hyaluronic acid, or a derivative of hyaluronic acid and reacting with an oxidant in the dark condition. In the process of the present invention, the aldehyde group introduced to the open-ring structure with maintaining a carboxyl group being capable of reacting with hyaluronic acid receptor, can be specifically bound with a protein as an active ingredient, thereby maximizing the transdermal delivery property of hyaluronic acid.

The oxidants applied for the present invention can be any oxidant inducing the ring-opening reaction, and preferably sodium periodate ($NaIO_4$).

In an embodiment, on the basis of unit of hyaluronic acid, a salt of HA or HA derivative, the oxidant can be reacted at an amount of 1 to 10 mole times for 2 to 24 hours, preferably 1 to 5 mole times for 2 to 12 hours. When the first step was performed by using the oxidant at 2 mole times for 3 hours, After the reaction of oxidant, the product can be purified by dialysis with a distilled water preferably.

The second step is to react the hyaluronic acid-aldehyde derivative obtained in the first step, with N-terminus of a water-soluble protein to produce a hyaluronic acid-protein conjugate represented by Chemical formula 2, and can be performed in a buffer solution of pH 5 to 7, preferably sodium acetate buffer solution of pH 5 to 6.5. The reaction pH used for the second conjugation step can prevent from hyaluronic acid-aldehyde an reacting an amino acid having amine group such as lysine, thereby obtaining the protein in a maximal activity, and increasing the bioconjugation efficiency and efficacy retention time.

Specifically, the hyaluronic acid-aldehyde is dissolved in a buffer solution, and then is reacted with a protein to form a bond between aldehyde group of hyaluronic acid-aldehyde derivative and an amine group at N-terminus of protein.

As a protein has an amine group at N-terminus, the protein can be used for the second step without additional preparing step for amine group. Preferably, the protein can be used as an aqueous solution of the dissolved protein.

The protein used for bio-conjugation with the hyaluronic acid-aldehyde derivative can be any protein being capable of dissolving in an aqueous solution without limitation. Preferably, the protein can be protein drug used for prevention or treatment of a disease and a skin-associated condition required for long-term periodic treatment, and for examples includes hGH, interferon-alpha, erythropoietin, TRAIL (Tumor necrosis factor-related apoptosis-inducing ligand) and insulin. The disease and skin-associated condition required for long-term periodic treatment includes dwarfism, cancer, diabetes, burn injury, atopic dermatitis, psoriasis, eczema, dermatitis, pimple, and herpes zoster preferably.

Preferably, the protein can be an antigen protein, for examples a protein, a recombinant protein, glycoprotein and peptide of pathogen.

The conjugate of the antigen protein and hyaluronic acid or derivative thereof stimulates Langerhans cell and dendritic cell as immune cells in skin tissue, and induces stronger immune response than only antigen protein (Experimental Example 15).

Preferably the protein can be used 1 to 10 molecules per a molecule of hyaluronic acid-aldehyde. The hyaluronic aldehyde group of hyaluronic acid-aldehyde, depending on the substitution degree, for the reaction of 12 to 24 hours.

Because the aldehyde group has a high reactivity, a third step can be further performed by blocking the remaining aldehyde group after the second step preferably. The blocking of the reaction with the unreacted aldehyde group can prevent the aldehyde group from reacting with other amine group of protein bound to the hyaluronic acid derivative, and non-specific reaction of the aldehyde group with the proteins in the body, after the hyaluronic acid-protein conjugate is introduced into the body, thereby preventing undesired reaction effectively and increasing the reaction efficiency.

Material used for the blocking step can be any material being capable of reacting with a carboxyl group or an aldehyde group without limitation, and preferably can be amines. The example of the blocking reaction is illustrated in Reaction scheme 2.

[Reaction scheme 2]

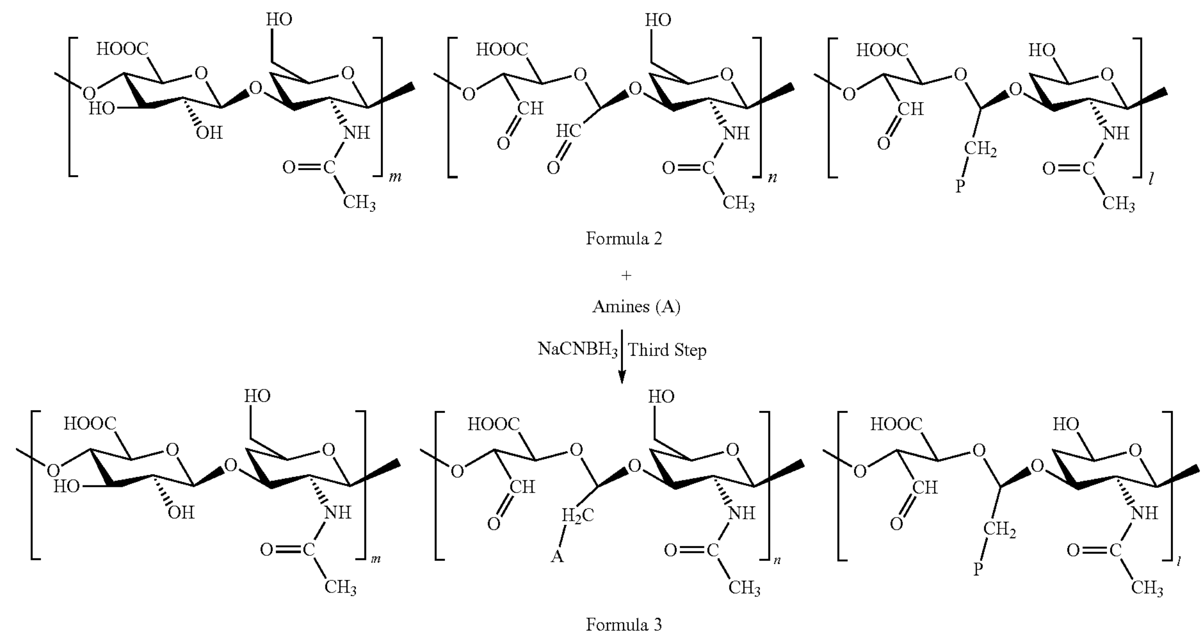

acid-protein conjugate with a binding ratio of 1 to 10 protein to 1 molecule of HA can be retained inside body for 24 hours to 96 hours, depending on the substitution degree of hyaluronic derivative acid, and can be used for drug delivery system of long-term. The hyaluronic acid-protein conjugate of the present invention can be applied for skin-associated disease and/or cosmetics due to the good transdermal delivery property, as well as various transdermal delivery systems of protein drugs.

In the method of an embodiment, the protein can be reacted with the addition of sodium cyanoborohydride (NaCNBH3) preferably. Sodium cyanoborohydride reduces the double bond occurred after the reaction of aldehyde group of HA derivative with N-terminal amine group of protein. Preferably, sodium cyanoborohydride can be added at an amount of 2 to 10 mole times as much mole of the The amines can be alkyl carbazates having C1 to C5 linear or branched chain, or lower alkanol amines having C1 to C5.

The alkyl carbazates are preferably ethyl carbazate or tert-butyl carbazate and the lower alkanolamines are for examples, aminomethanol (MEA), aminomethanol, 1-amino-2-propanol, 1-amino-3-propanol, aminobutanol and aminopentanol, and preferably aminoethanol.

When alkyl carbazates are used as the amines, the third step can be illustrated in Reaction scheme 3 and preferably can be performed by adding 5 to 10 mole times as much unit mole of aldehyde group in the compound of Chemical formula 2 and reacting for 12 to 24 hours, to produce the compounds represented by Chemical formula 3 where unreacted aldehyde group is blocked.

[Reaction scheme 3]

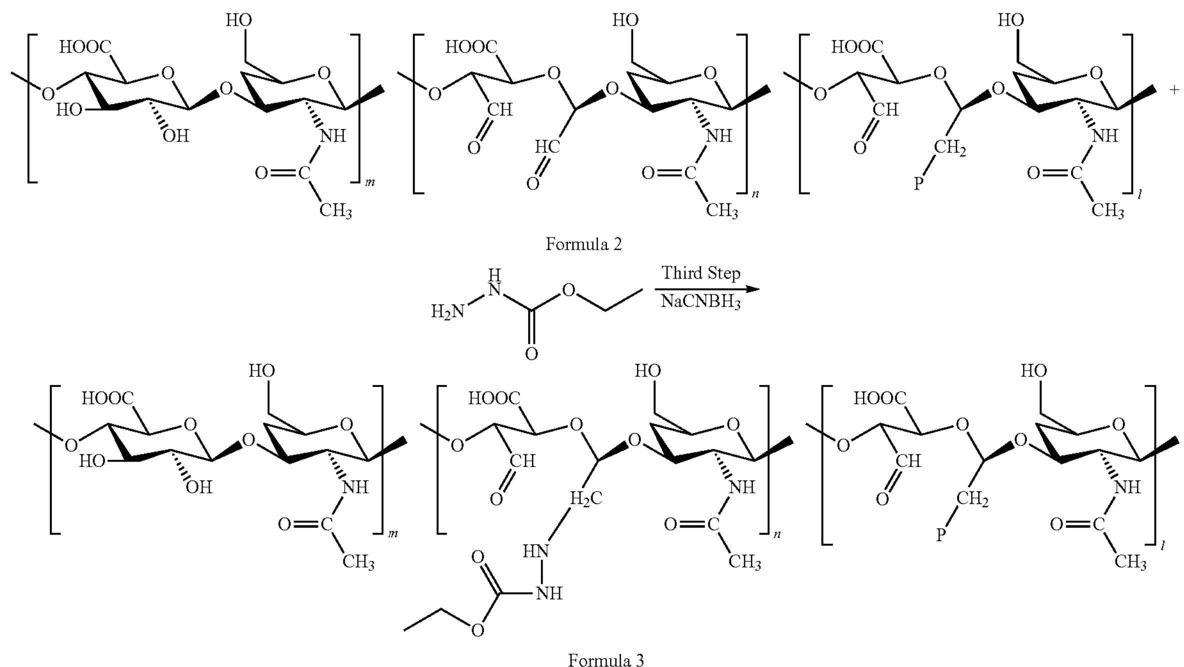

When alkanolamines are used as the amines, and preferably can be performed by adding 5 to 10 mole times as unit mole of aldehyde group in the compound of Chemical formula 2 and reacting for 12 to 24 hours.

The amounts of amines can block the reaction of unreacted aldehyde group completely. When the amines is added at a less than the amount, it is not preferable to guarantee the complete blocking.

When alkyl carbazates are used as the amines, the third step can be performed preferably at pH 5 to 7, and more preferably in acetate buffer solution of the first step.

When alkanolamines are used as the amines, the third step can be performed preferably at pH 7 to 9, and more preferably in phosphate buffer solution of the first step.

As described above, in the method of preparing hyaluronic acid-protein conjugate in accordance with the present invention, the conjugation reaction can be preferably in an aqueous solution, and can be applied for the preparation of drug delivery system for water-soluble peptide and protein being capable of dissolving in an aqueous solution by using the bioconjugation.

In an embodiment, the hyaluronic acid-protein conjugate represented by Chemical formula 2 is provided.

[Chemical formula 2]

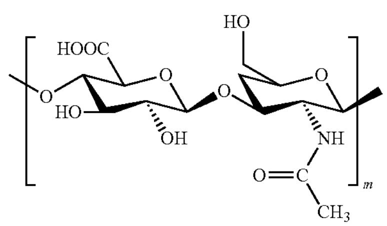

-continued

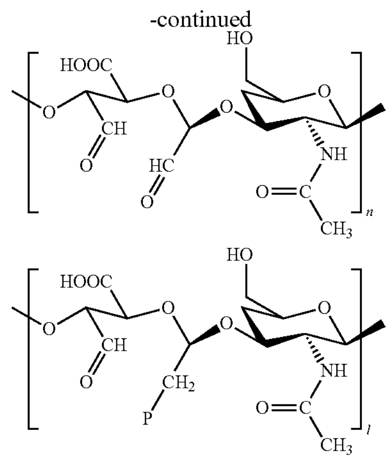

In chemical formula 2,

P is a water-soluble protein, the sum of m, n, and l is an integer of 50 to 10,000, the sum of n and l is an integer of 5 to 5,000, and l is an integer of 1 to 100.

The hyaluronic acid-protein conjugate is safe in body, and increases the biocompatibility of the protein having a maximal activity obtained by reacting with specific amino acid of protein and efficacy retention time, thereby providing an effective transdermal delivery system.

Hyaluronic acid is used for the wetting agent or wrinkle-improving agent in cosmetic. Because the skin cells such as keratinocyte in epidermis layer and fibroblast dermis layer have a receptor of hyaluronic acid, the growth of skin cells can be controlled by the concentration of hyaluronic acid. Various immune cells are in the skin tissue and can induce the immune reaction activation by stimulating the skin cells. Hyaluronic acid can be used for preparing a transdermal delivery vaccine composition with strong immune-stimulating activity. Thus, the hyaluronic acid-protein conjugate using hyaluronic acid having a transdermal property can be applied as a transdermal delivery system for an agent of treating a skin-associated diseases and protein drugs, cosmetics, vaccine and the like In an embodiment, a pharmaceutical composition for skin cell regeneration, a cosmetic composition and a vaccine composition for including the hyaluronic acid-protein conjugate at a therapeutically effective amount.

Herein, the term "therapeutically effective amount" means an amount being capable of causing a favorable effect or desired clinical or biochemical result, such as alleviating, improving, stabilizing, recovering, or delaying the progress of disease. The therapeutically effective amount can be administered at single dose or two or more dosages.

Preferably, the pharmaceutical composition, the cosmetic composition or the vaccine composition can further contain a pharmaceutically acceptable diluents or carriers, cosmetically acceptable diluents or carriers, or vaccinally acceptable diluents or carriers. The examples of diluents and carriers can be selected from those known to the skilled person in the art, such as excipients, additives, stabilizing agents and the like.

In an embodiment of the present invention, there is provided a method of delivering a hyaluronic acid-protein conjugate represented by Chemical formula 2, including a step of producing the hyaluronic acid-protein conjugate; and a step of administering a therapeutically effective amount of hyaluronic acid-protein conjugate to a subject in need.

The protein, the hyaluronic acid and the therapeutically acceptable amount are the same as described above, or can be adjusted by a skilled person in the art. The administration can be preferably transdermal administration, and the subject can be preferably mammal.

The hyaluronic acid-biodrug conjugate of the present invention can be conjugated in an aqueous solution, and thus can be applied for various water-soluble peptide and protein as the active ingredients and for simple and safe composition of protein drugs, cosmetics and vaccines, by maintaining the transdermal property of biocompatible biodegradable hyaluronic acid. In addition, the aldehyde derivative of hyaluronic acid can conjugate with N-terminal amine of protein at a specific pH condition and cannot react with other amines of protein. Thus, the protein in a maximal activity state can conjugate with HA derivative. The hyaluronic acid-protein conjugate of the present invention can be used effectively as an agent of treating skin-associated diseases, transdermal delivery system of protein drugs, cosmetics and vaccine.

The present invention is further explained in more detail with reference to the following examples. These examples, however, should not be interpreted as limiting the scope of the present invention in any manner.

EXAMPLE: PREPARATION OF HYALURONIC ACID-PROTEIN CONJUGATE

Example 1. HA-hGH Conjugate

HA (MW=100 kDa) was dissolved in water to be concentration of 10 mg/ml and reacted for 3 hours, 6 hours or 12 hours with the addition of sodium periodate ($NaIO_4$) at the same amount of one mole unit of HA under the dark condition. The reaction product was dialysis by using water with a dialysis membrane having 7,000 Da of molecular weight cutoff and then was freeze-dried for 3 days to obtain HA-aldehyde derivatives having the different substitution degrees.

The HA-aldehyde derivatives were dissolved in 100 mM acetate buffer solution (pH 5.5) to be concentration of 10 mg/ml, and added by aqueous solution of hGH provided by LG Lifescience to be 1 molecule, 4 molecules, 6 molecules or 8 molecules of reacted hGH per each 1 molecule (chain) of HA. Depending on the substitution degree of HA-aldehyde derivative, where the substitution degree was obtained according to the method of Experimental Example 1, Sodium cyanoborohydride ($NaCNBH_3$) was added at 5 mole times as much mole of the aldehyde group and reacted for 24 hours to produce the hyaluronic acid-protein conjugate. Then, the reaction product was added by ethyl carbazate at 5 mole times as much mole of aldehyde group in order to block the unreacted aldehyde group and reacted for two hours more. In case of using amino ethanol instead of ethyl carbazat, the reaction produced was added by amino ethanol at 5 mole times as mole of aldehyde group, adjusted to be pH 8 by adding NaOH, and then reacted for 12 hours more.

The produced solution was dialyzed with a phosphate buffered saline (PBS, pH 7.4) and stored at −70° C.

Example 2. HA-OVA Conjugate

HA (MW=215 kDa) was dissolved in water to be a concentration of 10 mg/ml and reacted for 3 hours with the addition of sodium periodate ($NaIO_4$) at the same amount of two mole times as much mole unit of HA under the dark condition. The reaction product was dialyzed by using water with a dialysis membrane having 7,000 Da of molecular weight cutoff and then was freeze-dried for 3 days to obtain HA-aldehyde derivatives having the different substitution degrees.

The HA-aldehyde derivatives were dissolved in 100 mM acetate buffer solution (pH 5.5) to be concentration of 8 mg/ml, and added by ovalbumin (Sigma-Aldrich) to be 3 molecules or 6 molecules of reacted OVA per each molecule (chain) of HA. Depending on the substitution degree of HA-aldehyde derivative, where the substitution degree was obtained according to the method of Experimental Example 1, Sodium cyanoborohydride ($NaCNBH_3$) was added at 5 mole times as much mole of the aldehyde group and reacted for 24 hours to produce the HA-protein conjugate. Then, the reaction product was added by ethyl carbazate at 5 mole times as much mole of aldehyde group in order to block the unreacted aldehyde group and reacted for two hours more. In case of using amino ethanol instead of ethyl carbazate, the reaction produced was added by amino ethanol at 5 mole times as much mole of aldehyde group, adjusted to be pH 8 by adding NaOH, and then reacted for 12 hours more.

The product was analyzed with GPC (Gel permeation chromatography) under GPC analyzing condition, to separate the HA-OVA from unreacted OVA, Sodium cyanoborohydride, ethyl carbazate and the like. The separated HA-OVA was concentrated with centrifuging filter at 5,000 rpm and then stored at −70° C.

<GPC Analysis Condition>

Pump: Waters 1525 binary HPLC pump

Absorbance detector: Waters 2487 dual λ absorbance detector

Sampler: Waters 717 plus auto-sampler

Column: (hGH) Waters Ultrahydrogel 500+Waters Ultrahydrogel 250

(OVA) Waters Ultrahydrogel 500+Waters Ultrahydrogel 1000 Mobile phase: PBS (pH 7.4)

Flow rate: 0.5 mL/min.

Measurement wavelength: dual detection at 210 nm and 280 nm

Experimental Example

1. Substitution Degree Analysis of HA Aldehyde Derivative

1) Analyzing Method

In order to analyze the substitution degree of the HA-aldehyde derivative produced in the preparing of HA-hGH conjugate in Example 1 and HA-OVA conjugate in Example 2, the produced HA-aldehyde derivative was dissolved in 100 mM acetate buffer solution (pH 5.2) to be concentration of 5 mg/ml HA, and was reacted for 25 hours with addition of tert-butyl carbazate (TBC) and sodium cyanoborohydride ($NaCNBH_3$) at 5 mole times per each unit of HA-aldehyde derivative, to produce the TBC bound to the aldehyde group in HA-aldehyde derivative (HA-aldehyde-TBC derivative). The product was dialyzed by using a distilled water for 3 days with MWCO 7000 dialysis membrane and was freeze-dried. The product was analyzed for the substitution degree with $^1$H-NMR (DPX300, Bruker, Germany).

2) Analyzing Result

Figure 1:
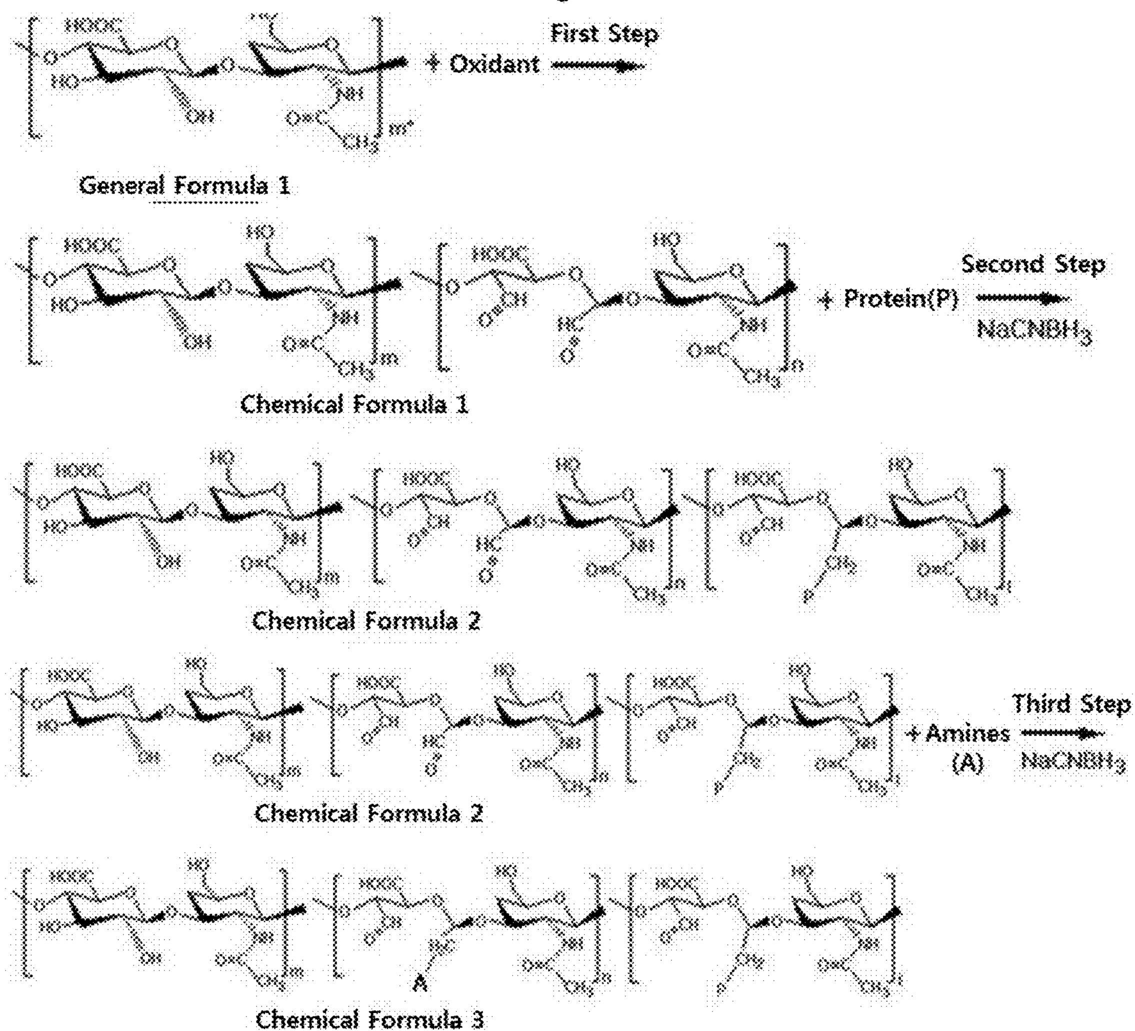
FIG. 1 is a schematic drawing showing a HA derivative including an aldehyde group and a method of preparing a HA-protein conjugate using the HA derivative, in accordance with an embodiment of the present invention.
Figure 2:
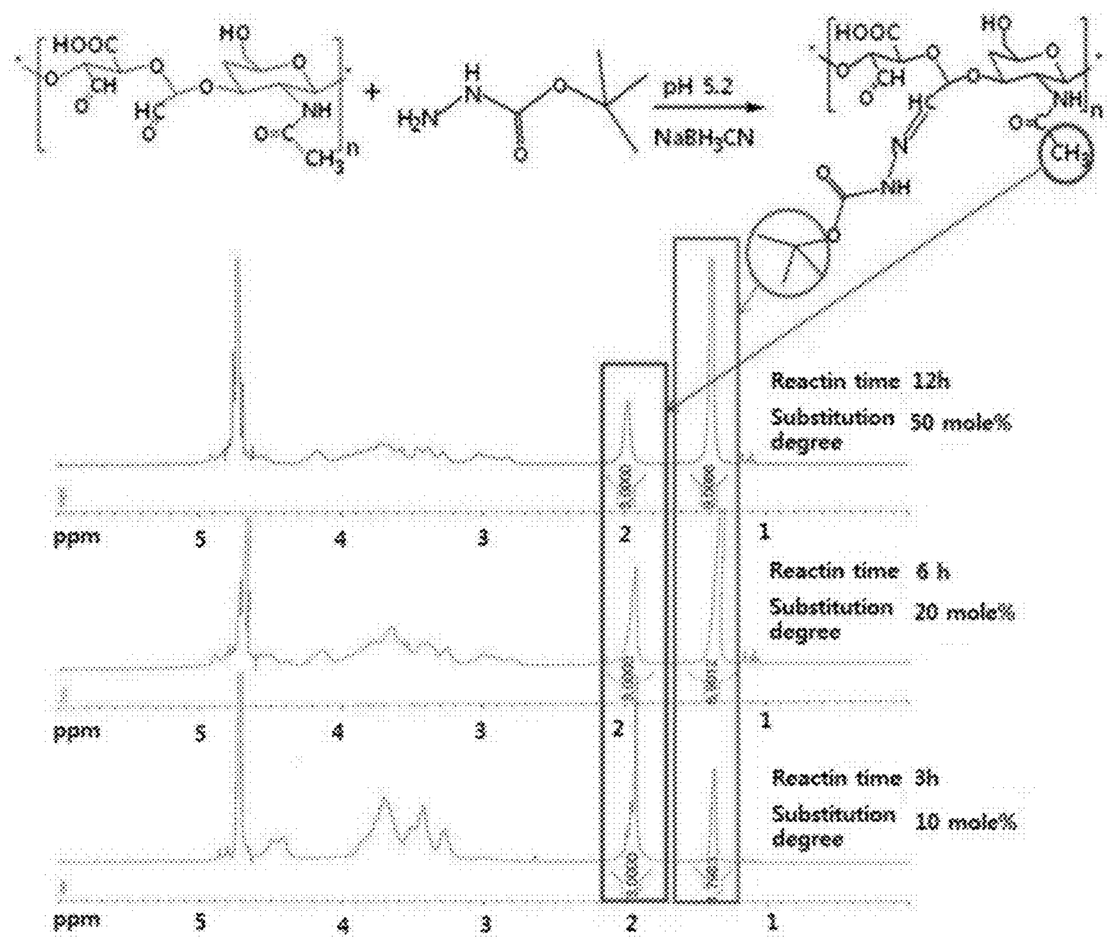
FIG. 2 is $^{1}$H-NMR analysis result of HA-aldehyde-TBC derivative which was prepared in accordance with an embodiment of the present invention.

As shown in FIG. 2, $^1$H-NMR spectrum of the HA-aldehyde-TBC derivative obtained item 1) represented a peak of HA and a peak of three methyl groups in TBC showing nine hydrogens at δ=1.2~1.4 ppm. For the quantitative analysis, the methyl resonance of acetamido moiety of HA at δ=1.85~1.95 ppm was determined as an internal standard.

The substitution degrees of HA-aldehyde derivatives of Example 1 and Example 2 were calculated from the peak area of δ=1.85~1.95 ppm and the peak area of δ=1.2~1.4 ppm. The $^1$H-NMR Analyzing result of the substitution degree of HA-aldehyde derivative confirmed that 10~50 mole % could be controlled by changing the reaction time of sodium cyanoborohydride. That is, as the reaction time was longer, the substitution degree of HA-aldehyde was higher. In the reaction of Example 1, when the reaction times were 3 hours, 6 hours and 12 hours, the reaction produced 10 mole %, 20 mole %, and 50 mole % of the substitution degree. In the reaction of Example 2, when the reaction time was 3 hours, it produced 15 mole % of substitution degree.

2. GPC Analysis of HA-Protein Conjugate

1) Analyzing Method

The formation of HA-protein conjugate was confirmed by GPC analysis for the HA-hGH conjugate obtained in Example 1 where HA-aldehyde derivative with about 10 mole % of substitution degree was obtained by reacting with $NaIO_4$ for 3 hours and was reacted with hGH at an amount of 6 mole times as much 1 mole of HA (100 kDa) at reaction rate: 95 mole % or higher), and HA-OVA conjugate obtained in Example 2 where HA-aldehyde derivative with about 15 mole % of substitution degree was obtained by reacting with $NaIO_4$ for 3 hours and was reacted with OVA at an amount of 3 mole times as much 1 mole of HA (215 kDa) at reaction rate: 80 mole % or higher. The GPC analysis of the HA-protein conjugate was performed with HPLC under the following analysis conditions.

<GPC Analysis Conditions>

Pump: Waters 1525 binary HPLC pump

Absorbance detector: Waters 2487 dual λ absorbance detector

Sampler: Waters 717 plus auto-sampler

Column: (hGH) Waters Ultrahydrogel 500+Waters Ultrahydrogel 250

(OVA) Waters Ultrahydrogel 500+Waters Ultrahydrogel 1000

Mobile phase: PBS (pH 7.4)

Flow rate: 0.5 mL/min.

Measurement wavelength: dual detection at 210 nm and 280 nm

2) Analyzing Result

As shown in FIG. 3*a*, the GPC analysis result of HA-hGH showed the peak of HA at 14 to 15 minutes and at a wavelength of 280 nm, which indicated the conjugation of protein to the HA. As shown in FIG. 3*b* of GPC analysis result of HA-OVA, the peak of OVA at 210 nm shifted to the direction of high molecular weight and was shown at 31~32 minutes, which confirmed the protein conjugation.

3. Quantitative Analysis of HA-Protein Conjugate

1) Analyzing Method

The protein content of HA-protein conjugates obtained in Examples 1 and 2 was calculated by measuring the peak area of GPC graph according to the GPC analyzing method of Experimental Example 2.

For analyzing HA-hGH, 1 mg/mL hGH solution was diluted with distilled water to prepare a hGH standard solution. The standard curve showing the peak area versus hGH concentration was obtained by analyzing the hGH standard solution under the analyzing condition of Experimental Example 2. The GPC peak area was obtained by analyzing HA-hGH conjugate of Example 1 according to the same method of hGH standard solution and was substituted the standard curve to produce hGH content in HA-hGH conjugate.

For analyzing HA-OVA, the standard curve showing the peak area versus OVA concentration was obtained according to the same method of HA-hGH analysis. The reacted OVA content was calculated from unreacted OVA concentration before the purification. As shown in FIG. 3*b*, unreacted OVA peak for the HA-OVA conjugate of Example 2 was shown at 36~37 minutes. The peak area was substituted the standard curve to obtained the unreacted OVA concentration in HA-OVA conjugate.

2) Analyzing Result

The content of protein (hGH) contained in HA-hGH conjugate obtained from Example 1 increased, as the molecule number of protein used for binding to one molecule of HA was higher. When the molecule number of protein per a molecule of HA increased to 1, 4, 6, and 8, the mean number of protein used for binding to one molecule of HA could be controlled to 1, 4, 6 and 8. Bioconjugation efficiency)(%) of the protein represented 95% or higher regardless of the number of protein (FIG. 4). Bioconjugation efficiency)(%) of HA-OVA conjugate obtained from Example 2 represented about 80% for 3 molecules of protein and about 65% for 6 molecules.

4. CD Analysis of HA-hGH Conjugate

1) Analyzing Method hGH solution (0.25 mg/ml) and HA-hGH conjugate solution were analyzed with Circular Dichroism (CD) by using hGH concentration as a reference. The analyzing condition of CD was shown as followings.

<CD Analysis Condition>

UV spectrophotometer: JASCO J-715

Measuring condition: 25 r, 200~250 nm, $N_2$ atmosphere quartz cuvette: 2 mm path length Raw data: 0.2 mm interval at reaction hour of 1 second 2) Analyzing Result As shown in FIG. 5, the CD peaks of hGH spectrum and HA-hGH conjugate were the same, which confirmed that the secondary structure of hGH was maintained in the conjugation with HA.

5. Analysis of the Activity of HA-hGH Conjugate

1) Analyzing method 1 mg/ml hGH solution was diluted with distilled water to obtain the dilute solutions with concentrations of 0.5, 1, 5, 10, 20, 30 or 50 ug/ml to prepare the standard solution of hGH, and the standard curve was obtained using Bradford assay. That is, the standard solution of hGH was mixed with Coomassie® Protein Assay Reagent at a mixing volumetric ratio of 1:1, and incubated at a room temperature for 10 minutes. The product was measured for absorbance at 595 nm to produce the standard curve.

The HA-hGH conjugate of Example 1 and the solution of hGH diluted at 100 times were analyzed under the same condition of standard curve according to Bradford assay, and the absorbance was substituted the standard curve to obtain the hGH content in the conjugate.

Then, hGH, each HA-hGH and the standard solution of hGH used for the Bradford assay were diluted at 1,000 times and the content of hGH was obtained by ELISA.

Specifically, 1 mg/ml of hGH standard solution was diluted to produce the reference solutions having the concentrations of 0, 1, 2, 5, 10, or 20 ng/ml. The samples were diluted with PBS to be concentrations of 0, 1, 2, 5, 10, or 20 ng/ml. 200 ul of each reference solutions and the sample diluents were loaded on 96 well plate pre-treated with hGH antibody and incubated at 37° C. for 1 hour. The well was washed with 250 ul/well of washing solution at five times, loaded with 200 ul/well of anti-hGH-DIG solution and incubated at 37° C. for 1 hour. Then the well plated was washed with 250 ul/well of washing solution at five times, treated with 200 ul/well of anti-DIG-POD secondary antibody), and incubated at 37° C. for 1 hour. The well plated was washed with 250 ul/well of washing solution at five times, added by 200 ul of POD substrate (peroxidase), and incubated for 20 minutes under the dark condition. The absorbance of well plate was detected at 405 nm. The detected absorbance value was substituted for the standard curve of reference solution and the concentration of sample interacting with the antibody. All materials used for ELISA were contained in hGH ELISA kit (roche).

The ratio of ELISA/Bradford assays analyzed the activity of HA-hGH conjugate.

2) Analyzing Result

As shown in FIG. 6*a*, the ratio of ELISA/Bradford assays for HA-hGH conjugate was 70% or higher.

Specifically, the Bradford assay uses the lysine of protein) and ELISA assay uses the interaction of hGH with the antibody interacting with hGH. The ratio of ELISA/Bradford assays provided the activity of HA-hGH conjugate. As shown in FIG. 6*a*, 70% or higher of the protein contained in the conjugate had the activities.

6. Analysis of Activity of HA-OVA Conjugate

1) Analyzing Method 1 mg/ml OVA solution was diluted with distilled water to obtain the dilute solutions with concentrations of 0.6, 1.2, 2.5, 5, 10, 20 ug/ml to prepare the standard solution of OVA. The standard curve using Bradford assay was obtained according to the same method of Experimental Example 5, except for the OVA solution instead of hGH solution.

The HA-OVA conjugate of Example 2 and OVA were diluted at 1,000 times. The absorbance was detected according to the same condition of Bradford assay and was substituted for the standard curve to obtain the OVA content.

Then, OVA, each HA-OVA and the standard solution of OVA used for the Bradford assay were diluted at 1,000 times and the OVA content was obtained by ELISA.

Specifically, 1 mg/ml of OVA standard solution was diluted to produce the reference solutions having the concentrations of 0, 0.6, 1.2, 2.5, 5, 10 or 20 ng/ml. The samples were diluted with PBS to be concentrations of 0 to 20 ng/ml. 50 ul of each reference solutions and the sample diluents were loaded on 96 well plate and incubated at 37° C. for 1 hour. The well was washed with 300 ul/well of washing solution at three times, loaded with 100 ul/well of anti-OVA-HRP solution (Thermo Scientific) and incubated at 37° C. for 1 hour at a room temperature. Then the well plated was washed with washing solution at three times, treated with 50 ul of TMB (3,3',5,5'-tetramethylbenzidine), and incubated at 37° C. for 20 minutes under the dark condition. The well plated was treated with stop solution (2N sulfuric acid), and the absorbance of well plate was detected at 450 nm. The detected absorbance value was substituted for the standard curve of reference solution and the concentration of sample interacting with the antibody. All materials used for ELISA were contained in hGH ELISA kit (roche).

The ratio of ELISA/Bradford assays analyzed the activity of HA-hGH conjugate.

2) Analyzing Result

As shown in FIG. 6*a*, the ratio of ELISA/Bradford assays for HA-OVA conjugate was 80% or higher. Specifically, the Bradford assay and ELISA assay were the same as explanation in Experimental Example 5. As shown in FIG. 6*b*, 80% or higher of the protein contained in the conjugate had the activities.

7. Serum Stability Analysis of HA-hGH Conjugate (In Vitro)

1) Analyzing Method

In order to test the serum stability of the HA-protein conjugate, hGH unbound to HA the following samples were used for the analysis.

HA-hGH conjugate (20/6: 20 mole % of substitution degree of aldehyde group and six hGH molecule bound per a molecule of HA)

The samples of HA-hGH conjugate and hGH were dissolved in the human serum (Sigma-aldrich) respectively to be concentration of 1 mg/mL of hGH and was incubated at 37° C. for 120 hours. After the time passed, a part of samples was obtained, diluted with PBS at 1,000 times in order to prevent the effect of human blood serum, and frozen. The biological activities of the samples were analyzed with hGH ELISA kit (roche) according to the manufacture's protocol.

2) Analyzing Result

As shown in FIG. 7, HA-hGH conjugate had higher stability than hGH for a longer time, and especially, the serum stability was higher, as the number of hGH bound to HA increased.

8. Cell Signaling Activity Test HA-hGH Conjugate (In Vitro)

1) Analyzing Method

IM-9 cell is human B lymphoblast and has hGH receptor, and thus the JAK2 (Janus kinase 2) is phosphorylated, if hGH binds to the receptor JAK2 (Janus kinase 2. The biological activity of HA-hGH was tested by using the property of IM-9 cell.

IM-9 cell (Korean cell line bank) was cultured in RPMI 1640(GIBCO) enriched with 10% (v/v) FBS and 25 mM HEPES. All cells were cultured in standard tissue culture dish which was stored in the maintaining condition of 5%

$CO_2$(g) and relative humidity at 37° C. incubator. IM-9 cells were treated with each concentration of hGH and cultured at 37° C. for 24 hours. Then, the phosphorylated JAK2 of cultured cells were analyzed quantitatively with Western blot method to confirm the hGH concentration showing the maximum cell signaling. At the same concentration of hGH, the cells were treated with the HA-hGH conjugate obtained in Example 1 and analyzed for the cell signaling activity (Laemmli, Nature, 227, 680-685 (1970)). The used antibody was purchased from santacruz biotechnology co.

2) Analyzing Result

As shown in FIG. 8A to 8C, at the treatment of 500 ng/ml of the hGH, the highest cell signaling activity was produced (FIG. 8 의 A). When HA-hGH conjugate including the same concentration of hGH was treated, the cell signaling activity was produced (FIG. 8 의 B). FIG. 8C was a graph showing the quantitative result of measuring the band intensity of the western blot result of FIG. 8A and FIG. 8B. Thus, the results confirmed that hGH bound to HA maintained its biological activity.

9. JAK2 Phosphorylation of the Human Skin Cell of Detroit 551 Cell Treated with hGH and HA-hGH Conjugate 1) Analyzing Method Human skin normal fibroblast of Detroit 551 (ATCC) was cultured in DMEM (GIBCO) enriched with 10% FBS and 25 mM HEPES. All cells were cultured in standard tissue culture dish which was stored in the maintaining condition of 5% $CO_2$(g) and relative humidity at 37° C. incubator. Detroit 551 cells were treated with about various concentrations of hGH and HA-hGH conjugate of Example 1 and cultured at 37° C. for 24 hours. Then, the phosphorylated JAK2 of cultured cells were analyzed quantitatively according to the same method of Experimental Example 7.

2) Analyzing Result

As described above, the phosphorylation of JAK2 occurred when hGH banded to hGH receptor.

As shown in FIG. 9A, at the treatment of hGH on Detroit 551 cells, the phosphorylation of JAK2 confirmed that the cell signaling caused by hGH receptor was occurred. As shown in FIG. 9B, at the treatment of HA-hGH conjugate on Detroit 551 cells, the phosphorylation of JAK2 confirmed that the cell signaling caused by hGH receptor was occurred. FIGS. 9C and 9D were a graph showing the quantitative result of measuring the band intensity of the western blot result of FIG. 9A and FIG. 9B. Thus, the results confirmed that the HA-hGH conjugate bonded to HA receptor and/or hGH receptor and showed the cell signaling activity.

10. The Growth of Human Skin Cell Line with Treatment of HA-hGH Conjugate

1) Analyzing Method

Human neonatal epidermal keratinocyte of HEKn cells (Invitrogen) were cultured in EpiLife medium (Invitrogen) enriched with 1% HKGS (human keratinocyte growth supplement. Detroit 551 cells (ATCC) was cultured in DMEM (GIBCO) enriched with 10% FBS and 25 mM HEPES. All cells were cultured in standard tissue culture dish which was stored in the maintaining condition of 5% $CO_2$(g) and relative humidity at 37 r incubator. The cells were seeded to 96-well plate at $3\times10^3$ cells per each well (A: HEKn B: Detroit 551) and incubated for 24 hours. Then, the well plated was treated with each different concentration of HA and HA-hGH conjugate of Example 1. To detect the cell growth degree, the cells were treated with WTS-1(TaKaRa) after 48 hours. When the mitochondrial dehydrogenase of the live cells transforms WTS-1(tetrazolium salt) to formazan, the absorbance change of medium solution is detected. The well plate treated with WST-1 was incubated at 37° C. for 1 hour and then the absorbance was detected at 450 nm.

2) Analyzing Result

As shown in FIG. 10, the cell growth was observed depending on the change in the concentration of HA-hGH conjugate.

When the cells were treated with 10 ug/ml of HA (high concentration), HEKn cells showed 20% of cell growth (A part of FIG. 10), and Detroit 551 cells showed 60% of cell growth (B part of FIG. 10). Excessive concentration of conjugated hGH can prevent the cell signaling of hGH, when it was used at a high concentration. Thus, HA-hGH conjugate was tested at a low concentration in order to detect suitably HA and hGH.

At a lower concentration of hGH, HEKn cells (C part of FIG. 10) having HA receptor but no hGH receptor showed the small difference at the increasing amounts of HA-hGH conjugate, but the Detroit 551 cells (D part of FIG. 10) having both HA receptor and hGH receptor showed higher growth at the concentration of HA-hGH conjugate increased. At the treatment of 500 ng/ml HA-hGH conjugate, which showed the maximum cell signaling activity, the highest cell growth was shown (about 40% growth).

11. Pharmacokinetic (PK) Analysis of HA-hGH Conjugate (In Vivo)

1) Analyzing Method 300 ul of each PBS, hGH and HA-hGH conjugate solution including 1 mg/ml hGH was injected into SD rat (female, 6-weeks, 200 g) through tail vein and after certain time interval, the blood was collected from the tail vein and was analyzed for the blood concentrations of samples by using hGH ELISA kit (roche).

2) Analyzing Result

As shown in FIG. 11, the blood concentration of hGH was dropped below the baseline before 24 hours, but was maintained at high level when it was provided with the HA-hGH conjugate form. Especially, when the HA-hGH conjugate (20/6) which included the 20% of high substitution degree of aldehyde group was used, the blood concentration of hGH was not dropped below the baseline. The result confirmed that the long blood half-life of protein drug could cause the efficacy retention time, when the protein drug was provide in the conjugate form of present invention.

12. The Properties Analysis of Transdermal Drug Delivery System Using HA-hGH Conjugate 1) Analyzing Method Hairless Balb/c mouse (female, 6-weeks, 20 g) and PBS, FITC (fluorescein isothio-cyanate), hGH-FITC, HA-FITC, HA-hGH-FITC conjugate were prepared.

hGH-FITC and HA-hGH-FITC conjugate with tagging FITC were prepared by dissolving FITC in 2 mg/ml phosphate buffer (pH 9) and reacting for 3 hours with hGH at a concentration of 5 mole times FITC of hGH. Then, the unreacted FITC was removed with PD10 column.

To react with FITC, Free HA without amine group was firstly bound with Hexamethylenediamine in the present of EDC catalyst to introduce the amine group and then reacting with FITC according to the same method of HA-hGH. The prepared samples were applied to 1 cm×1 cm area of mouse back skin at a concentration of 100 ul of 1 mg/ml FITC. After 1 hour, the skin tissue was obtained and fixed using OCT compound. The fixed skin tissue was cryosectioned at a thickness of 30 um and detected by using the tissue fluorescence analysis with confocal microscopy to obtain the transdermal penetrating efficiency of the samples.

2) Analyzing Result

As shown in FIG. 12(A: control, B: FITC, C: hGH-FITC, D: HA-FITC, E: HA-hGH-FITC), FITC hGH (B) and hGH-FITC (C) which did not bind to HA, did not penetrate the skin tissue layer and the fluorescence was detected only in external part of skin tissue. However, HA-FITC (D) and HA-hGH-FITC (E) bound to HA, showed the uniform distribution of fluorescence in the skin tissue and confirmed that HA had a transdermal delivery property. The analysis result confirmed that HA derivative bound to hGH of water-solution protein (E) also represented the good transdermal efficiency.

13. The Properties Analysis of Transdermal Drug Delivery System Using HA-OVA Conjugate 1) Analyzing Method Hairless Balb/c mouse (female, 6-weeks, 20 g) and PBS, FITC (fluorescein isothio-cyanate), OVA-FITC, HA-FITC, HA-OVA-FITC conjugate were prepared.

OVA-FITC and HA-OVA-FITC conjugate with tagging FITC were prepared by dissolving FITC in 2 mg/ml phosphate buffer (pH 9) and reacting for 3 hours with OVA solution at a concentration of 10 mole times FITC of OVA concentration. Then, the unreacted FITC was removed with PD10 column.

To react with FITC, Free HA without amine group was firstly bound with Hexamethylenediamine in the present of EDC catalyst to introduce the amine group and then reacting with FITC according to the same method of HA-OVA. The prepared samples were applied to 1 cm×1 cm area of mouse back skin at a concentration of 100 ul of 1 mg/ml FITC. After 1 hour, the skin tissue was obtained and fixed using OCT compound. The fixed skin tissue was cryosectioned at a thickness of 30 um and detected by using the tissue fluorescence analysis with confocal microscopy to obtain the transdermal penetrating efficiency of the samples.

2) Analyzing Result

As shown in FIG. 13(A: PBS, B: FITC, C: OVA-FITC, D: HA-FITC, E: HA-OVA-FITC), FITC (B) and OVA-FITC (C) which did not bind to HA, did not penetrate the skin tissue layer and the fluorescence was detected only in external part of skin tissue. However, HA-FITC (D) and HA-OVA-FITC (E) bound to HA, showed the uniform distribution of fluorescence in the skin tissue and confirmed that HA had a transdermal delivery property. The analysis result confirmed that HA derivative bound to hGH of water-solution protein (E) also represented the good transdermal efficiency.

14. Pharmacokinetic (PK) Analysis of HA-hGH Conjugate (In Vivo)

1) Analyzing Method

After the back skin of SD rat (female, 6-weeks, 200 g) was shaved, 3 cm×3 cm area of hairless back skin was treated with 300 ul of each PBS, hGH, HA-hGH conjugate at a concentration of 1.5 mg/ml hGH. After certain time interval, the blood was collected from the tail vein and was analyzed for the blood concentrations of samples by using hGH ELISA kit (roche). To compare the result with the subcutaneous injection, the same volume of HA-hGH conjugate was injected into the rat subcutaneously and the blood concentrations of samples were analyzed at various time intervals according to the same method.

2) Analyzing Result

As shown in FIG. 14, hGH unbound to HA did not penetrate into the skin tissue and showed the blood concentration below the baseline. Because of the transdermal penetration of HA-hGH conjugate (10/6), its blood concentration reached Cmax of 20 ng/ml and hGH was detected in the blood. Thus, when hGH was delivered transdermal in a form of the HA-hGH conjugate. hGH could penetrate into the skin tissue layer and delivered into the blood.

The transdermal delivery system had 20% bioavailability of the subcutaneous injection system and suggested that the transdermal delivery system had very good delivery efficiency, in considering the lower delivery efficiency of transdermal delivery system than the subcutaneous injection due to the skin penetration. In addition, only skin application achieved 20% delivery efficiency of subcutaneous injection, by considering the patient compliance. In particular, the transdermal delivery system had many advantages for the diseases such as dwarfism required the long-term treatment.

15. Property Analysis of Transdermal Vaccine Using HA-OVA Conjugate (In Vivo)

1) Analyzing Method

After the back skin of Balb/c mouse (male, 8-weeks, 200 g) was shaved, 1 cm×1 cm area of hairless back skin was treated with 50 ul of each PBS, OVA, HA-OVA conjugate at a concentration of 10 mg/ml OVA. After two and four weeks of transdermal delivery, the blood was collected from the tail vein and was analyzed for the blood concentrations of samples by using OVA ELISA kit (roche).

Specifically, the 96-well plate well was loaded with OVA for 1 hour and washed with 300 ul/well three times. Mouse anti-OVA antibody standard solution Sigma Aldrich) was diluted at 0, 3, 6, 12.5, 25, 50, 100, 200 ng/ml as a reference solution. The samples were diluted with PBS to be concentration of 0 to 20 ng/ml. The well plate was treated with 50 ul of each reference solution and the dilute sample solutions and incubated at a room temperature 1 hour. The well plate was washed with 300 ul/well three times, loaded with 100 ul/well of goat anti-mouse IgG antibody-HRP solution (Millipore) and incubated at a room temperature for 1 hour. The well plate was washed three times, and treated with 50 ul of TMB (3,3',5,5'-tetramethylbenzidine), and incubated at 37° C. for 20 minutes under the dark condition. The well plated was treated with 50 ul of stop solution (2N sulfuric acid), and the absorbance of well plate was detected at 450 nm. The detected absorbance value was substituted for the standard curve of reference solution to measure the blood concentration of anti-OVA IgG antibody.

2) Analyzing Result

As shown in FIG. 15, when OVA and HA-OVA were delivered transdermal at the same volume and concentration, OVA delivered in a form of HA-OVA conjugate produced 5 times higher concentration of antibody at two weeks, and 15 times as high as the concentration of antibody at four weeks, compared to the antibody concentration of free OVA. The result suggested that HA-OVA conjugate penetrated into the epidermal and dermal skin tissue more efficiently than free OVA. HA-OVA conjugate penetrated into the deep skin tissue and induced the immune cells such as Langerhans cell and dendritic cell in skin tissue, thereby efficiently causing an immune response. As a result, the HA-vaccine conjugates such as HA-OVA conjugate could increase the antibody production notably due to the excellent transdermal delivery property. Thus, the HA-vaccine conjugates can improve the patient's convenience and the vaccination effect and applied for good vaccine delivery system.

What is claimed is:

1. A method of transdermal delivery for a protein comprising:

administering a hyaluronic acid-protein conjugate which is represented by having Chemical formula 2 to a subject in need thereof:

[Chemical formula 2]

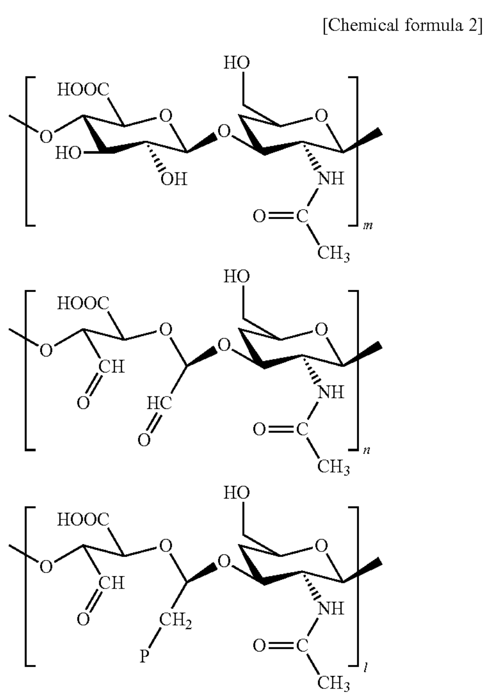

in chemical formula 2,

P is a water-soluble protein, the sum of m, n, and l is an integer of 50 to 10,000, the sum of n and l is an integer of 5 to 5,000, and l is an integer of 1 to 100, wherein the hyaluronic acid-protein conjugate is obtained by reacting the hyaluronic acid-aldehyde(HA-aldehyde) compound represented by Chemical formula 1 with N-terminus of a water-soluble protein:

[Chemical formula 1]

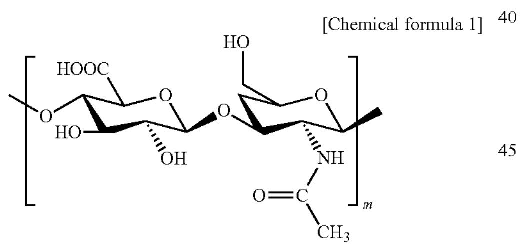

-continued

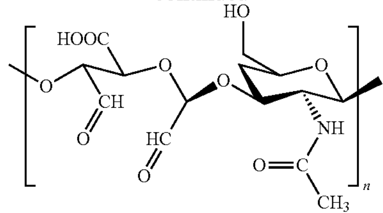

in chemical formula 1, the sum of m and n is an integer of 50 to 10,000, and n is an integer of 5 to 5,000, and the hyaluronic acid-aldehyde compound has a aldehyde substitution degree of 10 to 50 mole %; and the hyaluronic acid-protein conjugate includes 1 to 10 molecules of protein bound to a molecule of the hyaluronic acid-aldehyde compound, wherein the water-soluble protein is human growth hormone, erythropoietin, Tumor necrosis factor-related apoptosis-inducing ligand (TRAIL), or ovalbumin, wherein blood is collected from the subject and blood concentration of the hyaluronic acid-protein conjugate is determined and the transdermal delivery has 20% bioavailability compared to a subcutaneous injection.

2. The method of claim 1, wherein the reaction of hyaluronic acid-aldehyde(HA-aldehyde) compound represented by Chemical formula 1 with N-terminus of a water-soluble protein is performed in a buffer solution having a pH 5 to 7.

3. The method of claim 1, wherein the hyaluronic acid-aldehyde compound is obtained by opening a cellulose ring of the hyaluronic acid(HA), by reacting a salt of hyaluronic acid or a derivative of the hyaluronic acid with an oxidant.

4. The method of claim 1, wherein the hyaluronic acid (HA) has a molecular weight of 10,000 to 3,000,000 Da.

5. The method of claim 4, wherein an oxidant is reacted for 2 to 24 hours with the hyaluronic acid at an amount of 1 to 10 mole times the amount of the hyaluronic acid.

6. The method of claim 1, wherein the subject is mammal.

* * * * *